US005578574A

United States Patent [19]

Shuman et al.

[11] Patent Number: 5,578,574
[45] Date of Patent: Nov. 26, 1996

[54] ANTITHROMBOTIC AGENTS

[75] Inventors: Robert T. Shuman, Greenwood; Robert B. Rothenberger, Brownsburg; Kenneth D. Kurz, Indianapolis; Daniel J. Sall, Greenwood; Gerald F. Smith, Indianapolis; Michael R. Wiley, Indianapolis, all of Ind.

[73] Assignee: Eli Lilly and Company, Indianapolis, Ind.

[21] Appl. No.: 397,452

[22] Filed: Mar. 2, 1995

Related U.S. Application Data

[63] Continuation of Ser. No. 206,554, Mar. 4, 1994, abandoned.

[51] Int. Cl.$^6$ .............................. A61K 38/00; C07K 5/00; C07K 7/00; C07K 17/00

[52] U.S. Cl. .............................. 514/18; 514/19; 530/331; 540/476; 544/372; 544/111; 544/141; 544/58.5; 548/146; 548/215; 548/240; 548/214; 548/468

[58] Field of Search .......................... 530/331; 514/18–19; 540/476; 544/372, 111, 141, 58.5; 548/146, 215, 240, 214, 468

[56] References Cited

U.S. PATENT DOCUMENTS

| | | | |
|---|---|---|---|
| 4,316,889 | 2/1982 | Bajusz et al. | 424/177 |
| 4,346,078 | 8/1982 | Bajusz et al. | 424/177 |
| 4,399,065 | 8/1983 | Bajusz et al. | . |
| 4,478,745 | 10/1984 | Bajusz et al. | . |
| 4,703,036 | 10/1987 | Bajusz et al. | 514/18 |
| 5,053,392 | 10/1991 | Klein et al. | 514/18 |
| 5,153,176 | 10/1992 | Abe et al. | 514/18 |
| 5,202,416 | 4/1993 | Steuber et al. | 530/322 |
| 5,204,323 | 4/1993 | Findlay et al. | 514/2 |
| 5,250,660 | 10/1993 | Shuman et al. | 530/344 |
| 5,252,566 | 10/1993 | Shuman et al. | 514/210 |
| 5,380,713 | 1/1995 | Balasubramanian et al. | 514/18 |
| 5,416,093 | 5/1995 | Shuman | 514/307 |
| 5,430,023 | 7/1995 | Gesellchen et al. | 514/18 |
| 5,436,229 | 7/1995 | Ruterbories et al. | 514/18 |
| 5,439,888 | 8/1995 | Shuman et al. | 514/18 |
| 5,484,772 | 1/1996 | Sall et al. | 514/18 |
| 5,488,037 | 1/1996 | Sall et al. | 514/19 |

FOREIGN PATENT DOCUMENTS

| | | |
|---|---|---|
| A-16380/95 | 4/1995 | Australia . |
| A-21801/95 | 6/1995 | Australia . |
| 0293881 | 12/1988 | European Pat. Off. . |
| 0410411 | 1/1991 | European Pat. Off. . |
| 0479489 | 4/1992 | European Pat. Off. . |
| 0526877 | 8/1992 | European Pat. Off. . |
| 504064 | 9/1992 | European Pat. Off. . |
| 0503203 | 9/1992 | European Pat. Off. . |
| 0529568 | 3/1993 | European Pat. Off. . |
| 0530167 | 3/1993 | European Pat. Off. . |
| 0542525 | 5/1993 | European Pat. Off. . |
| 648780 | 8/1994 | European Pat. Off. . |
| 4117396 | 4/1992 | Japan . |
| WO93/08211 | 4/1993 | WIPO . |
| WO93/15756 | 8/1993 | WIPO . |
| WO94/29335 | 12/1994 | WIPO . |
| WO94/29336 | 12/1994 | WIPO . |
| WO95/09859 | 4/1995 | WIPO . |
| WO95/09858 | 4/1995 | WIPO . |
| WO95/09634 | 4/1995 | WIPO . |

OTHER PUBLICATIONS

Bajusz, S., et al., *J. Med. Chem.*, 1990, 33, 1729–1735.
Fareed, J., et al., *Annals N.Y. Academy of Sciences*, 1981, 765–784.
Shuman, et al., Proceedings of the Twelfth American Peptide Symposium, Jun. 16–21, 1991, pp. 799–802.
Wilson, et al., American Heart Association, Nov. 11–14, 1991, Anaheim Convention Center, Anaheim, CA, Abstract.
Bajusz, et al., *Int. J. Peptide Res.*, 12, 1978, 217–221.
Gesellchen, et al., Tenth American Peptide Symposium, May 23–28, 1987, St. Louis, MO.
Claeson, et al., Proceedings of the Twelfth American Peptide symposium, Jun. 16–21, 1991, Cambridge, MA, pp. 824–825.
Smith, G. F., Shuman, R. T. Gesellchen, P. D., Craft, T. J., Gifford, P., Kurz, K. D., Jackson, C. V., Sandusky, G. E., and P. D. Williams, A New Family of Thrombin Inhibitors with Improved Specificity and Therapeutic Index. (Submitted to the American Heart Association, Oct., 1991, Circulation Oct., 1991, vol. 84, II–579, 1991), Abstract.
Jackson, V., Wilson, H., Frank, J., Crowe, V., Craft, T., and G. Smith. The Thrombin Inhibitor, Methyl–D–Phe–Pro–Arginal—An Effective Adjunct to Coronary Artery Thrombolysis in the Anesthetized Dog. FASEB J. 5(4)A520 (1991).
Crowe, V., Frank, J., Wilson, H., Coffman, B., Smith, G., and V. Jackson. Anticoagulant and Antithrombotic Efficacy of the Novel Thrombin Inhibitor Methyl–D–Phg–Pro–Arginal in a Canine Model of Coronary Thrombosis. FASEB J. 5(4)A520 (1991).
Wilson, H., Frank J., Crowe, V., Coffman, B., Smith, G., Shuman, R., and V. Jackson. Anticoagulant and Antithrombotic Efficacy of the Novel Thrombin Inhibitor, Methyl–D––Phg–Pro–Arginal, in a Canine Model of Coronary Thrombosis (Arteriosclerosis and Thrombosis, 11(5), Oct., 1991) p. 1586a.

(List continued on next page.)

*Primary Examiner*—Toni R. Scheiner
*Assistant Examiner*—Sheela J. Huff
*Attorney, Agent, or Firm*—Thomas E. Jackson; John C. Demeter; David E. Boone

[57] ABSTRACT

This invention relates to L-arginine aldehyde derivatives, having the formula I $$X-Y-\underset{\underset{H}{\overset{|}{C=O}}}{\overset{H\ H}{\underset{|}{N}}-\overset{|}{\underset{*}{C}}}-(CH_2)_3-\overset{H}{\underset{|}{N}}-\overset{NH}{\underset{|}{C}}-NH_2 \quad \text{I}$$

where X and Y have the values defined in the description, as well as pharmaceutical formulations containing those compounds and methods of their use as thrombin inhibitors, coagulation inhibitors, and thromboembolic disorder agents.

25 Claims, No Drawings

OTHER PUBLICATIONS

Jackson, V., Wilson, H., Frank, J., Crowe, V., Coffman, B., Shuman, R., and G. Smith. the Novel Thrombin Inhibitor Methyl–D–Phg–Pro–Arginal: An Effective Conjunctive Agent to Coronary Artery Thrombolysis in the Anesthetized Dog. (Arteriosclerosos and Thrombosis, 11(5), Oct., 1991) p. 1586a.

Shuman, R. T., Rothenberger, R. B., Campbell, C. S., Smith, G. F., Jackson, C. V., Kurz, K. D., and P. D. Gesellchen. Prevention of Reocclusion by a Thrombin Inhibitor. (American Peptide Symposium, Jun., 1991, pp. 799–800).

Shuman, R. T., Rothenberger, R. B., Campbell, C. S., Smith, G. F., Jackson, C. V., Kurz, K. D., and P. D. Gesellchen. A Series of Highly Active Serine Proteinase Inhibitors.(American Peptide Symposium, Jun. 1991, pp. 801–802).

Jackson, C. V., Frank, J. D., Crowe, V. G., Craft, T. J., and G. F. Smith. Assessment of the Anticoagulant and Antithrombotic Efficacy of the Thrombin Inhibitor, BOC–Phe–Pro–Arginal, in a Canine Model of Coronary Thrombosis. *Arteriosclerosis*, 10 922A (1990).

Jackson, C. V., Frank, J. D., Crowe, V. G., Craft, T. J., and G. F. Smith. the Thrombin Inhibitor, BOC–D–Phe–Pro–Arginal. An Effective Adjunct to Coronary Artery Thrombolysis in the Anesthetized Dog. *Arteriosclerosis*, 10 923a (1990).

Shackelford, K. A., Tanzer, R. L., Shuman, R., Gesellchen, P. D., Grindey, G. B., Sundboom, J. L., Smith, G. F., and R. L. Merriman. Inhibition of Spontaneous Metastasis by Boc–D–Phe–Pro–Arginal. American Association for Cancer Research, San Francisco, 1989. *Proc. Am. Assn. Cancer Res.*, 30 86, 1989.

Neubauer, B. L., Clemens, J. A., Gesellchen, P. D., Hirsch, K. S., Hoover, D. M., Merriman, R. L., and G. F. Smith. Endocrine Characterization and Sensitivity of the PAIII Prostatic Adenocarcinoma in Male Lobund–Wistar (LW) Rats to Anti–Fibrin Agents. American Association for Cancer Research. New Orleans, May 1988, *Proc. Am. Assn. Cancer Res.*, 29 240 (1988).

Neubauer, B. L., Best, K. L., Gesellchen, P. D., Goode, R. L., Merriman, R. L., Tanzer, L. R., Shaar, C. J., Shuman, R., Sundboom, Pro–Arginal of the Metastasis of the PAIII Prostatic Adenocarcinoma in Male Lobund Wistar (LW) Rats. American Urological Association. Boston, May 1988, *J. Urol.*, 139 175A (1988).

Gesellchen, P. D., Smith, G. F., et al., Anticoagulant, Antithrombotic, and Antimetastatic Effects of a Serine Proteinase Inhibitor. 10th American Peptide Symposium, Washington University, St. Louis, MO (1987), Abstract.

Smith, G. F., Sundboom, J. L., Best, K., Gesellchen, P. D., Merriman, R. L., Shuman, R., and Neubauer, B. L. Heparin, Boc–D–Phe–Pro–Arginal, and Warfarin (Fibrin Antagonists) Inhibit Metastasis in an In Vivo Model. American Chemical Society National Meeting. Abstract BIOL 70 Biochemistry (1987).

K. D. Kurz, T. Smith, R. A. Moore, and B. W. Main. Comparison of Thrombin Inhibitors in Rat Models of Thrombosis and Thrombolysis. FASEB Journal, vol. 5 (No. 4), 1991, Abstract #886.

Tomori, et al., *Chromatographia*, vol. 19, 437–442 (1984).

Dayhoff, *Atlas of Protein Sequence and Structure*, 5, pp. 85–89 (1972).

Shuman, et al., *J. Med. Chem.*, 36(3), 314–319 (1993).

Jackson, et al., *J. Cardiovasc. Pharmacol.*, 21(4), 587–594 (1993).

Cheng, et al., *Tetrahedron Lett.*, 32 (49), 7333–7336 (1991).

Bagdy, et al., *Thrombosis and Haemostasis*, 68(2), 125–129 (1992).

*Thrombosis and Haemostasis*, 65, 1289, Nos. 2150–2151 and 2152 (1991).

Bagdy, et al., *Thrombosis and Haemostasis*, 67(3), 325–330 (1992).

Bagdy, et al., *Thrombosis and Haemostasis*, 67(3), 357–365 (1992).

Balasubramanian, et al., *J. Med. Chem.*, 36, 300–303 (1993).

Shuman, et al., Oral Activity of Tripeptide Aldehyde Thrombin Inhibitors, Thirteenth American Peptide Symposium, Jun. 20–25, 1993, Abstract.

Kurz et al., Antithrombotic Efficacy in the Rat After Intravenous and Oral Administration of a Direct Inhibitor of Thrombin FASEB, Mar. 28–Apr. 1, 1993.

Iwanowicz, et al., *Bioorg. Med. Chem. Lett.*, 2(12), 1607–1612 (1992).

Barabas, et al., *Blood Coagul. Fibrin.*, 4, 243–248 (1993).

Jackson, et al., Conjunctive Therapy with the Thrombin Inhibitor, LY 294468, and Aspirin Produced Enhanced Antireocclusive Activity When Used in a Canine Model of Streptokinase–Induced Coronary Thrombolysis, *The Pharmacologist*, 35(3), 207 (1993), Abstract #407.

Pozagay, et al., Study of the Specificity of Thrombin with Tripeptidyl–p–Nitroanilide Substrates, *Eur. J. Biochem.*, 115, 491–495 (1981).

Jackson, et al., *The Journal of Pharmacology and Experimental Therapy*, 261(2), 546–552 (1992).

Stueber, et al., Proc. of the 13th American Peptide Symposium, Jun. 20–25, 1993.

Stürzebecher, et al., XIVth Congress of the International Society on Thrombosis and Hemostasis, Jul. 4–9, 1993.

Simoons et al., *Circulation*, 90, I–231, Abstr. 1241 (1994).

ANTITHROMBOTIC AGENTS

This is a continuation-in-part of application Ser. No. 08/206,554, filed Mar. 4, 1994 and now abandoned.

This invention relates to thrombin inhibitors which are useful anticoagulants in mammals. In particular it relates to L-arginine aldehyde derivatives having high anticoagulant activity, antithrombotic activity, and oral bioavailability.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation.

Anticoagulation is currently achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because surface-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest in small synthetic peptides that are recognized by proteolytic enzymes in a manner similar to that of natural substrates has grown. Tripeptide aldehydes such as D-Phe-Pro-Arg-H, Boc-D-Phe-Pro-Arg-H, and D-MePhe-Pro-Arg-H, Bajusz et al., *J. Med. Chem.*, 33, 1729–1735 (1990) demonstrate potent direct inhibition of thrombin. Many investigators have synthesized analogs in an effort to develop pharmaceutical agents, for example Shuman et al., *J. Med. Chem.*, 36, 314–319 (1993), as well as European Patent Applications, publication numbers 479489 and 542525. Early clinical studies which demonstrate that D-MePhe-Pro-Arg-H sulfate is an anticoagulant in man have been reported, see Simoons et al., *Circulation*, 80, I-231, Abstr. 1241 (1994).

Although the heparins and coumarins are effective anticoagulants, and no drug has yet emerged from the known tripeptide aldehydes, and despite the continuing promise for this class of compounds, there exists a need for anticoagulants that act selectively on thrombin, and independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent thrombin inhibitors that have high bioavailability following oral administration.

Accordingly, it is a primary object of the present invention to provide novel L-arginine aldehyde derivatives that are potent thrombin inhibitors useful as anticoagulants.

Other objects, features and advantages will be apparent to those skilled in the art from the following description and claims.

The present invention provides a thrombin inhibiting compound having the formula I

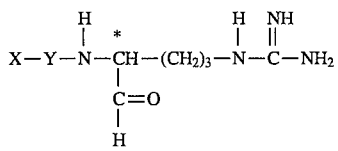

wherein

X is an unsubstituted or substituted group selected from homoprolinyl, prolinyl, thiazolidinoyl, isothiazolidinoyl, thiomorpholinoyl, piperazinoyl, morpholinoyl, oxazolidinoyl, isoxazolidinoyl, 2-azanorbornoyl, and fused bicyclic rings

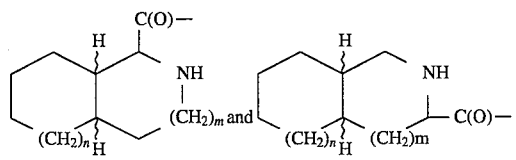

where n is 1—3 and m is 2 or 3 and in a sulfur containing group the sulfur may be oxidized with one or two oxygen atoms;

Y is

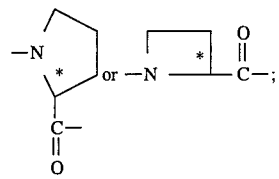

or a pharmaceutically acceptable salt thereof or a pharmaceutically acceptable solvate of said compound or salt thereof.

In addition to the compounds of formula I, the present invention provides pharmaceutical formulations comprising a compound of formula I in association with a pharmaceutically acceptable carrier, diluent or excipient.

The present invention also provides a method of inhibiting coagulation in mammals comprising administering to a mammal in need of treatment, a coagulation inhibiting dose of a compound of formula I.

The present invention further provides a method of inhibiting thrombin comprising administering to a mammal in need of treatment, a thrombin inhibiting dose of a compound of formula I.

Further, the present invention provides a method of treating a thromboembolic disorder comprising administering to a mammal in need of treatment, an effective dose of a compound of formula I.

This invention relates to new inhibitors of thrombin, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process.

The term "alkyl" by itself or as part of another substituent means a straight or branched chain alkyl radical having the stated number of carbon atoms such as methyl, ethyl, n-propyl, isopropyl, n-butyl, t-butyl, isobutyl and sec-butyl.

The term "alkoxy" means a straight or branched chain alkyl radical having the stated number of carbon atoms bonded to the parent moiety by an oxygen atom. The term "halo" means chloro, fluoro, bromo or iodo. The term "di($C_1$-$C_4$ alkyl)amino" means a group —N($C_1$-$C_4$ alkyl)$_2$ where each alkyl group, independently, has the stated number of carbon atoms.

The group

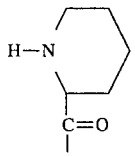

is referred to at times herein as homoprolinyl and abbreviated hPro.

The term "azetidine" refers to an azetidine-2-carbonyl group and is abbreviated Azt. The terms "thiazolidinoyl, isothiazolidinoyl, thiomorpholinoyl, piperazinoyl, morpholinoyl, oxazolidinoyl, and isoxazolidinoyl" refer to the stated ring group having a carbonyl functionality bonded thereto so as to afford a stable structure.

The term "2-azanorbornoyl" means a group

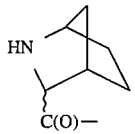

When X is a substituted group, including the fused bicyclic ring groups, there can be one to three of the same or different substituents that will afford a stable structure selected from halo, hydroxyl, $C_1$-$C_4$ alkyl, $C_1$-$C_4$ alkoxy, amino (—NH$_2$), mono($C_1$-$C_4$ alkyl) amino, di($C_1$-$C_4$ alkyl)amino, mercapto, $C_1$-$C_4$alkylthio (—S(O)$_p$($C_1$-$C_4$ alkyl)), —NHS(O)$_p$($C_1$-$C_4$ alkyl), —NHC(O)$C_1$-$C_4$ alkyl, —S(O)$_p$NH2, —S(O)$_p$NH($C_1$-$C_4$ alkyl), —S(O)$_p$N($C_1$-$C_4$ alkyl)$_2$, substituted or unsubstituted phenoxy, substituted or unsubstituted naphthyloxy, substituted or unsubstituted pyridyloxy, substituted or unsubstituted phenylthio; p is 0, 1 or 2; and the substituents on the phenoxy, naphthyloxy, pyridyloxy and phenyl thio groups are one or two of the same or different substituents selected from halo, hydroxyl, $C_1$-$C_4$ alkyl, $C_1$-$C_4$ alkoxy, amino (—NH$_2$), mono($C_1$-$C_4$ alkyl)amino, di($C_1$-$C_4$ alkyl) amino, mercapto, $C_1$-$C_4$alkylthio (—S(O)$_p$($C_1$-$C_4$ alkyl)), —NHS(O)$_p$($C_1$-$C_4$ alkyl), —NHC(O)$C_1$-$C_4$ alkyl, —S(O)$_p$NH2, —S(O)$_p$NH($C_1$-$C_4$ alkyl), —S(O)$_p$N($C_1$-$C_4$ alkyl)$_2$, and p is 0, 1 or 2.

In the representation of formula I, the carbonyl functionality of group X is attached to the amine functionality of the Y group. The carbonyl functionality of Y is attached to the amino group drawn in Formula I.

The asterisks in formula I and substituent Y denote a chiral center that is (L).

In addition, diastereomers exist at the X substituent and, depending on substitutions on said X substituent, further diastereomers may exist. The compounds of the present invention include mixtures of two or more diastereomers as well as each individual isomer.

The following compounds illustrate compounds contemplated within the scope of formula I:

D-homoprolinyl-L-prolinyl-L-arginine aldehyde;
D-Prolinyl-L-prolinyl-L-arginine aldehyde;
D-homoprolinyl-L-azetidin-2-carbonyl-L-arginine aldehyde;
D-Prolinyl-L-azetidin-2-carbonyl-L-arginine aldehyde; and
D-(4-Phenoxy)prolinyl-L-prolinyl-L-arginine aldehyde.

Preferred compounds of the present invention are those compounds of formula I where X is unsubstituted or monosubstituted homoprolinyl, unsubstituted or monosubstituted prolinyl, unsubstituted or monosubstituted piperazinoyl, or an unsubstituted or monosubstituted fused bicyclic ring selected from

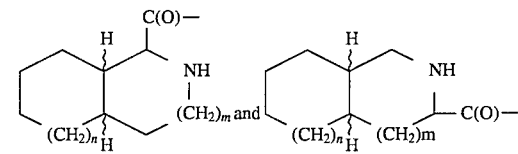

where n and m and Y are as defined above for formula I, and pharmaceutically acceptable salts and solvates thereof.

Particularly preferred compounds of the present invention are those compounds of formula I where X is homoprolinyl, prolinyl, 4-phenoxyprolinyl, piperazinoyl, or a fused bicyclic ring selected from

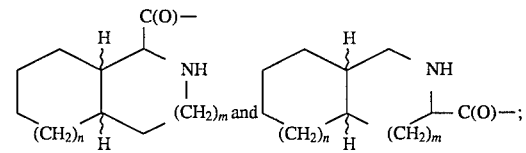

where n, m and Y are as defined above for formula I; and pharmaceutically acceptable salts or solvates thereof.

As mentioned above, the invention includes pharmaceutically acceptable salts of the compounds defined by the above formula I. A particular compound of this invention can possess one or more sufficiently basic functional groups, and accordingly react with any of a number of nontoxic inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluene sulfonic, methanesulfonic acid, oxalic acid, p-bromo phenyl sulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid, hydrobromic acid and sulfuric acid.

As stated above, the present invention includes solvates of the compounds of formula I and the pharmaceutically acceptable salts thereof. A particular compound of the present invention or a pharmaceutically acceptable salt thereof may form solvates with water or common organic solvents. Such solvates are included within the scope of compounds of the present invention.

A compound of formula I is prepared by removing simultaneously or sequentially the protecting group(s) P of a corresponding compound of Formula II

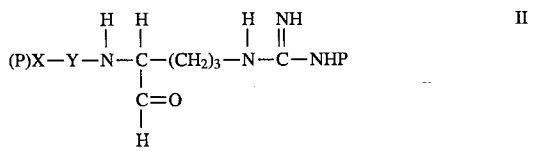

wherein P on the guanidino group represents an amino protecting group and (P)X represent a radical X, which may bear an independently selected amino protecting group P for a compound of formula I in which X includes a basic NH moiety; whereafter, when a salt of the compound of formula I is required, forming the salt with a pharmaceutically acceptable acid. For example, a compound of Formula II in which the amino protecting group(s) is (are) benzyloxycarbonyl may be converted into the hydrochloride of the corresponding compound of formula I by hydrogenolysis at atmospheric pressure over palladium on carbon catalyst in dilute ethanolic hydrochloric acid.

The compounds of formula I are prepared by known methods of peptide coupling. According to one such method the acid PX—COOH, where X—COOH is the acid equivalent of the X groups as defined for formula I, and P is an amino protecting group, is coupled with a carboxy protected proline (or azetidine-2-carboxy ester) to form the dipeptide. The carboxy protecting ester group of the proline moiety is then removed (deblocked or deesterified) and the free acid form of the dipeptide is coupled with the lactam form of arginine. The above reaction sequence is illustrated by the following Scheme 1:

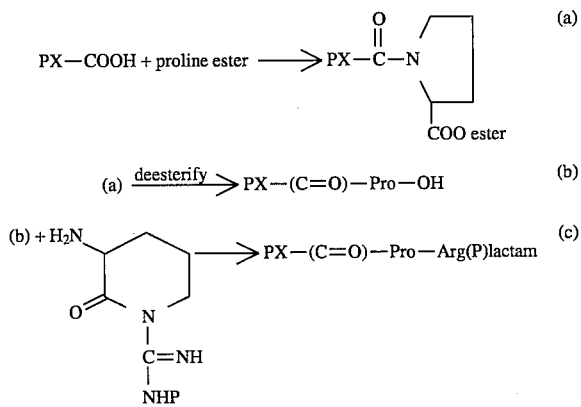

wherein P represents an amino protecting group.

The coupled Arg(P) lactam product (c) is reacted with a hydride reducing agent, preferably lithium aluminum hydride or lithium tri-tert-butoxyaluminohydride, in an inert solvent or mixture of solvents to reduce the lactam ring and provide the tripeptide in the arginine aldehyde form represented by the formula

wherein (P) represents amino protecting groups.

The protecting groups are removed by procedures known to those skilled in the art such as hydrogenation over a metal catalyst.

The lactam form of arginine is obtained by intramolecular coupling of amino protected arginine [Arg-OH]. For example, Boc-Arg(Cbz)OH, represented by the formula

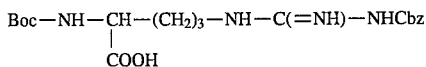

where Boc is t-butyloxycarbonyl and Cbz is benzyloxycarbonyl, is first converted to an active ester form, such as an active mixed anhydride, with a chloroformate ester, e.g. ethyl chloroformate to isobutyl chloroformate. The ester formation is carried out in the presence of a tertiary amine such as N-methylmorpholine. Addition of further or another tertiary amine base, such as triethylamine or diisopropylethylamine, effects the internal acylation to provide the lactam form of the di-amino protected arginine as shown below

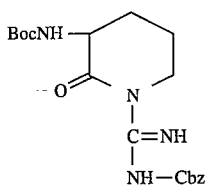

Prior to use in the coupling with the PX(C═O)-Pro-OH as shown in the above scheme, the Boc or other amine protecting group is selectively removed with trifluoroacetic acid or HCl to provide the requisite free amino group.

The coupling of a PXCOOH compound with a proline ester, when X is as defined above for formula I, is carried out by first protecting the amino group of the amino acid. Conventional amino protecting groups commonly used for temporary protection or blocking of the amino group are employed.

The amino-protecting group refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, t-butoxycarbonyl 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluoroenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichlorethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group, and the like amino-protecting groups. The species of amino-protecting group employed is not critical so long as the derivatized amino group is stable to the condition of subsequent reaction(s) on other positions of the molecule and can be removed at the appropriate point without disrupting the remainder of the molecule. Preferred amino-protecting groups are the benzyloxycarbonyl, allyloxycarbonyl, t-butoxycarbonyl, and trityl groups. Similar amino-protecting groups used in the cephalosporin, penicillin and peptide art are also embraced by the above terms. Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

In carrying out the coupling reaction, an ester protecting group for proline is employed which is removable by conditions under which the amino protecting group remains intact. The amino protecting group of the acylating acid PXCOOH thus remains in place for protection of the amino group during the subsequent coupling with the arginine lactam compound to form (c) in Scheme 1.

The carboxy protecting ester group as used in the specification refers to one of the ester derivatives of the carboxylic acid group commonly employed to block or protect the carboxylic acid group while reactions are carried out on other functional groups on the compound. Examples of such carboxylic acid protecting groups include $C_1$–$C_4$ alkyl, benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, 2-(trimethylsilyl)ethyl, 2-(di(n-butyl)methylsilyl)ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the conditions of subsequent reaction(s) on other positions of the molecule and can be removed at the appropriate point without disrupting the remainder of the molecule. In particular, it is important not to subject the carboxy-protected molecule to strong nucleophilic bases or reductive conditions employing highly activated metal catalysts such as Raney nickel. (Such harsh removal conditions are also to be avoided when removing amino-protecting groups discussed below.) Preferred carboxy protecting groups are $C_1$–$C_3$ alkyl and benzyl. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The compounds of formula I where Y is azetidinyl (or prolinyl) are prepared in an analogous manner by known methods of peptide coupling. According to one such method, the cyclic lactam form of arginine (e) is prepared and coupled with an amino protected azetidine-2-carboxylic acid (d) as shown below to afford the dipeptide (f)

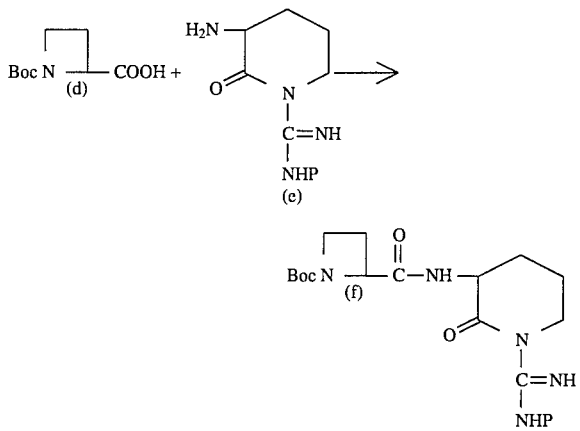

where P represents an amino protecting group such as the benzyloxycarbonyl (Cbz) group, t-butoxycarbonyl (Boc), p-toluenesulfonyl, and the like. Preferably the amino protecting group used is removable by hydrogenation or treatment with mild acid (e.g. trifluoroacetic acid) or a strong acid (e.g. HCl). Examples of other suitable amino protecting groups are provided in "Protective Groups in Organic Synthesis", Second Edition, by T. W. Greene and Peter G. M. Wuts, Chapter 7, page 309–405 (1991), John Wiley & Sons, Inc., publishers. The Boc, or other suitable protecting group, is removed from the azetidine ring nitrogen which is then acylated with the desired amino acid acyl group to afford the tripeptide shown below.

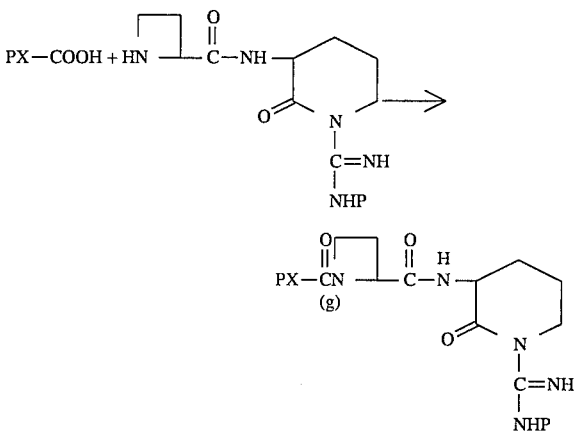

Although illustrated and described for those compounds of the present invention where Y is azetidinyl-2-carbonyl, one skilled in the art will appreciate these procedures can also be used to afford those compounds of the present invention where Y is prolinyl.

The coupled Arg(P) lactam product (g) is reduced with a hydride reducing agent, preferably lithium aluminum hydride or lithium tri-tert-butoxyaluminohydride, in an inert solvent or mixture of solvents to reduce the lactam and provide the tripeptide in the arginine aldehyde form represented by the formula PX(C=O)-Azt-Arg(P)-H wherein P represents an amino protecting group. The protecting groups are removed by procedures known to those skilled in the art such as hydrogenation over a metal catalyst.

Alternatively, the compounds of the invention are prepared by coupling the PXCOOH acid with carboxy protected azetidine-2-carboxylic acid. The carboxy is deprotected as the dipeptide which is then coupled with the amino protected arginine in the lactam form prepared as described above. The tripeptide is then reduced to provide the amino protected arginal tripeptide as described above.

The coupling of an PXCOOH compound is carried out by first protecting the amino group of the amino acid. Conventional amino protecting groups commonly used for temporary protection or blocking of the amino group are employed. Examples of such protecting groups are described above.

The coupling reactions described above are carried out in the cold preferably at a temperature between about −20° C. and about 15° C. The coupling reactions are carried out in an inert organic solvent such as dimethylformamide, dimethylacetamide, tetrahydrofuran, methylene chloride, chloroform, and like common solvents or a mixture of such solvents. Generally anhydrous conditions are used when, in the coupling reaction, an active ester of the acylating acid is used.

The compounds of the invention are isolated best in the form of acid addition salts. Salts of the compounds of formula I formed with acids such as those mentioned above are useful as pharmaceutically acceptable salts for administration of the antithrombotic agents and for preparation of formulations of these agents. Other acid addition salts may be prepared and used in the isolation and purification of the peptides. For example, the salts formed with the sulfonic acids such as methanesulfonic acid, n-butanesulfonic acid, p-toluenesulfonic acid and naphthalenesulfonic acid may be so used.

The preferred method for purifying the compounds of formula I, while at the same time preparing a desired stable salt form, is that described in U.S. Pat. No. 5,250,660. According to the method, stable sulfates or hydrochlorides are provided by preparative purification over $C_{18}$ reversed-phase chromatography in which the aqueous component comprises sulfuric acid or hydrochloric acid at pH 2.5 and acetonitrile is the organic component. The pH of the acidic eluant is adjusted to between about pH 4 and about 6 with an anion exchange resin in the hydroxyl form, e.g. Bio-Rad AG-1X8. After adjustment of the pH, the solution of tripeptide sulfate or hydrochloride salt is lyophilized to provide the pure salt in dry powder form. In an example of the process, crude D-hPro-L-Azt-L-Arg-H sulfate is dissolved in water and the solution is loaded on Vydac $C_{18}$ RPHPLC 5 cm×50 cm column. A gradient of 2–20 percent B (A=0.01 percent $H_2SO_4$; B=acetonitrile) over 10 hours is used. Multiple fractions are collected and those containing product as determined by analytical RPHPLC are pooled. The pH of the pooled fractions is adjusted to pH 4.0–4.5 with AG-1X8 resin in hydroxide form (Bio-Rad, 3300 Ragatta Blvd., Richmond, Calif. 94804). The solution is filtered and the filtrate is X-8790A -16lyophilized to provide the pure D-,L-,L- tripeptide in the form of the sulfate salt.

The optically active isomers of the diastereomers of the X substituent are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds employed as initial starting materials in the synthesis of the compounds of this invention are well known and, to the extent not commercially available, are readily synthesized by standard procedures commonly employed by those of ordinary skill in the art.

The following Examples are provided to further describe the invention and are not to be construed as limitations thereof.

The $R_f$ values in the following examples unless otherwise stated, were determined by silica gel thin layer chromatography using Kieselgel 60F-254 (Merck, Darmstadt) in the following solvent systems:

(A) chloroform-methanol-acetic acid, 135:15:1, v:v:v (B) ethyl acetate-acetic acid-absolute ethanol, 90:10:10, v:v:v (C) chloroform-methanol-acetic acid, 90:30:5, v:v:v The analytical HPLC methods used in the examples were as follows:

Method 1. Waters 600E using a Vydac $C_{18}$ reversed-phase column of 0.46 cm×10 cm. The chromatogram was monitored on an LDC at 214 nM using a gradient of A=water containing 0.1 percent (v:v)TFA and B=acetonitrile containing 0.1 percent (v:v) TFA.

Method 2. Pharmacia FPLC using a Vydac $C_{18}$ reversed-phase column measuring 0.46 cm×10.0 cm. Monitoring was done on a Pharmacia UV-M at 214 nM using a gradient of either A=water containing 0.1 percent (v:v) TFA or B=acetonitrile containing 0.1 percent (v:v) TFA.

Method 3. Hitachi L-6200 using a Vydac $C_{18}$ reversed-phase column of 0.46 cm×10 cm. Samples were eluted using a gradient composed of A (0.1% (v:v) aqueous TFA) and B (0.1% TFA in acetonitrile). The chromatogram was monitored at 214 nm using a L-4000 UV detector.

The abbreviations used in the examples have the following meanings.

Amino acids: Ar=arginine, Pro=proline, hPro=homoproline, Azt=azetidine-2-carboxylic acid, Phe=phenylalamine, hPhe=homophenylalanine Boc=t-butyloxycarbonyl (t-butoxycarbonyl)

Bzl=benzyl

Cbz=benzyloxycarbonyl

DCC=dicyclohexylcarbodiimide

DMF=dimethylformamide

DMSO=dimethylsulfoxide

EtOAc=ethyl acetate $Et_2O$=diethyl ether

EtOH=ethanol

FAB-MS=fast atom bombardment mass spectrum

FD-MS=field desorption mass spectrum

HOBT=1-hydroxybenzotriazole hydrate

HPLC=High Performance Liquid Chromatography

IR=Infrared Spectrum

LAH=Lithium Aluminum Hydride

NMR=Nuclear Magnetic Resonance

MOC=methoxycarbonyl

RPHPLC=Reversed Phase High Performance Liquid Chromatography

TFA=trifluoroacetic acid
THF=tetrahydrofuran
TLC=thin layer chromatography

Unless otherwise stated, pH adjustments and work up are with aqueous acid or base solutions.

EXAMPLE 1

Preparation of D-Homoprolinyl-L-Prolinyl-L-Arginine Aldehyde Dihydrochloride (D-hPro-Pro-Arg-H.2HCl)

A) Cbz-D-homoproline

D-Pipecolic acid (5.0 g, 38.7 mmol) was dissolved in tetrahydrofuran (100 mL) and water (30 mL). The pH of the solution was adjusted to 9.5 with 2N NaOH, and benzyl chloroformate (5.5 mL, 38.7 mmol) was added dropwise and the pH maintained at 9.5 with 2N NaOH. The reaction was stirred for an additional 1 hour at room temperature. The organic solvent was evaporated in vacuo, diethyl ether (100 mL) and water (50 mL) were added to the residue. The aqueous layer was separated, the pH of the solution was adjusted to 2.8 with 3N HCl and ethyl acetate (150 mL) was added. The organic layer was separated and dried (MgSO$_4$); the filtrate was concentrated in vacuo to give a clear oil of the title compound (9.6 g; 95 percent yield):

FD-MS 264 (MH$^+$);
TLC R$_f$ (A) 0.37;
$^1$HNMR (CDCl$_3$) δ1.22–1.58 (m, 2H), 1.60–1.80 (m, 2H), 2.20–2.35 (m, 1H), 2.98–3.18 (m, 1H), 4.00–4.20 (m, 1H), 4.85–5.05 (m, 1H) 5.20 (s, 2H), 7.30–7.40 (d, 5H);
$[\alpha]_D$ +39.0° (C=0.5/MeOH).

B) Cbz-D-homoprolinyl-Proline

Cbz-D-homoproline (A) (9.5 g, 36 mmol) was dissolved in EtOAc (100 mL) and the solution cooled to 0° C. Added to the solution was 2,4,5 trichlorophenol (7.1g, 36 mmol) and dicyclohexylcarbodiimide (7.4 g, 36 mmol). The reaction was stirred for 1 hour at 0° C. and 1 hour at room temperature. The precipitate was filtered and the filtrate concentrated in vacuo to an oil. The oil was dissolved in pyridine (100 mL), L-proline (4.2 g, 36 mmol), and triethylamine (5.0 mL, 36 mmol) were added. The reaction was stirred at room temperature (24 hours). The reaction solvent was removed in vacuo to an oil. The residue was dissolved in water (100 mL), diethyl ether (50 mL) was added and the pH adjusted to 9.5 with 2N NaOH. The aqueous layer was extracted twice with diethyl ether. The aqueous layer was separated, the pH adjusted to 2.8 with 3N HCl and EtOAc (150 mL) was added. The organic layer was separated, dried (MgSO$_4$), and the filtrate evaporated in vacuo to an amorphous solid (11.4 g; 88 percent yield);

FD-MS 361 (MH$^+$);
TLC R$_f$ (A) 0.78;
$[\alpha]_D$=−2.7° (C=0.5/Trifluoroethanol);

Elemental Analysis calculated for C$_{19}$H$_{24}$N$_2$O$_5$: C 63.32, H 6.71, N 7.77; Found: C 63.42, H 6.84, N 7.96.

C) Boc-Arg(Cbz)-OH

Boc-Arg(HCL)-OH (82.1 g, 250 mmol) was dissolved in 5N NaOH (240 mL) in a 3 necked flask. The reaction mixture was chilled to −5° C. and the pH was maintained at 13.2–13.5 using 5N NaOH (250 mL) while adding benzyl chloroformate (143 mL, 1.0 mol) dropwise (55 min). The reaction mixture was stirred for an additional 1 hour at −5° C. and diluted with H$_2$O (100 mL) and Et$_2$O (500 mL). The aqueous layer was separated and extracted with Et$_2$O (2×500 mL). The aqueous layer was acidified to pH 3.0 with 3N H$_2$SO$_4$ (560 mL) and extracted with EtOAc (550 mL). The aqueous layer was separated and extracted once with EtOAc. The combined EtOAc layers were washed with water and dried (MgSO$_4$). The organic layers were concentrated to dryness in vacuo to give the title compound (66.1 g; 65 percent yield):

TLC R$_f$ (C) 0.43;
FD-MS 408 (M$^+$);
$^1$HNMR (CDCl$_3$) δ1.42 (s,9H), 1.61–1.91 (m,4H), 3.23–3.41 (m,2H), 4.17 (d, 1H), 5.21 (s,2H), 5.62 (d, 1H), 7.30–7.42 (m, 6H), 8.37 (m, 1H).

D) Boc-Arg(Cbz)-Lactam

Boc-Arg(Cbz)-OH (C) (66.0 g, 0.162 mol) was dissolved in THF (230 mL) and cooled to −10° C. To the reaction mixture was added N-methylmorpholine (18.7 mL, 0.17 mol) followed by isobutyl chloroformate (22.5 mL, 0.17 mol). The reaction mixture was stirred 5 minutes at −10° C. and triethylamine (23.5 mL, 0.17 mol) was added. The reaction mixture was stirred for 1 hour at −10° C. and 1 hour at room temperature. The reaction mixture was poured into 1 L of ice-water and the resulting precipitate filtered, washed with cold water, and dried in vacuo. The product was crystallized from EtOAc to give the title compound (38.05 g; 60 percent yield):

TLC R$_f$ (A) 0.77;
FD-MS 391 (MH$^+$);
$^1$HNMR (CDCl$_3$) δ1.48 (s, 9H), 1.78–1.98 (m, 2H), 2.50 (m, 1H), 3.41 (m, 1H), 4.43 (m, 1H), 4.90 (m, 1H), 5.16 (s, 2H), 5.27 (m, 1H), 7.28–7.45 (m, 6H), 9.41 (m, 1H), 9.68 (m, 1H).

E) HCl.Arg(Cbz)-Lactam

A solution of HCl(g) saturated in EtOAc (7.2 L) was added dropwise over 30 minutes to a solution of Boc-Arg(Cbz)-Lactam (D) (641 g, 1.64 mol) dissolved in CH$_2$Cl$_2$ (3 L) at −10° C. The reaction was allowed to stir 1 hour at −10° C. and slowly warmed to room temperature over 3 hours. Diethyl ether (12 L) was added and the precipitate was filtered, washed with diethyl ether, dried (MgSO$_4$) and concentrated to dryness in vacuo to give the title compound (580 g):

TLC R$_f$ (C) 0.29;
FD-MS 291 (MH$^+$).

F) Cbz-D-hPro-Pro-Arg(Cbz)-Lactam

In flask 1 Cbz-hPro-Pro-OH (B) (11.1 g, 30.8 mmol) was dissolved in DMF (75 mL), cooled to −15° C. and N-methylmorpholine (3.4 mL, 30.8 mmol) was added followed by isobutyl chloroformate (4.0 mL, 30.8 mmol). The reaction mixture was stirred at −15° C. for 2 minutes.

In flask 2 HCl.Arg(Cbz)-Lactam (E) (10.1 g, 30.8 mmol) was dissolved in DMF (75 mL), cooled to 0° C., and diisopropylethylamine (10.7 mL, 61.6 mmol) was added. The reaction mixture was stirred at 0° C. for 2 minutes.

The contents of flask 2 were added to flask 1 in one portion and the reaction mixture was stirred for 4 hours at −15° C. The reaction mixture was slowly warmed to room temperature (24 hours). To the reaction mixture was added 1N NaHCO$_3$ (5 mL) and the reaction solvent was removed in vacuo. To the oil was added EtOAc (200 mL) and water (100 mL), the organic layer was separated, washed with 1N NaHCO$_3$, water, 1.5N citric acid, and water. The organic layer was dried (MgSO$_4$), and the filtrate evaporated to an amorphous solid of the title compound (17.4 g, 89 percent yield):

TLC R$_f$ (A) 0.66;

FAB-MS 633 (MH$^+$).

G) Cbz-D-hPro-Pro-Arg(Cbz)-H

Cbz-D-hPro-Pro-Arg(Cbz)-Lactam (F) (17.2 g, 27.1 mmol) was dissolved in anhydrous THF (200 mL) and placed in a flask under a N$_2$ atmosphere. The reaction mixture was cooled to −65° C. and lithium aluminum hydride 1M in THF (27.1 mL, 27.1 mmol) was added dropwise over 5 minutes. The reaction mixture was stirred at −65° C. for 30 minutes. A solution of 5 mL of THF and 5 mL of 0.5N H$_2$SO$_4$ was added dropwise to the reaction mixture over 5 minutes. The reaction mixture was diluted with EtOAc (150 mL), and water (50 mL) and the organic layer separated. The organic layer was washed with water (2×100 mL) and dried (MgSO$_4$). The filtrate was concentrated to dryness in vacuo to an amorphous solid to give the title compound (14.1 g; 82 percent yield):

TLC R$_f$ (A) 0.33;

FAB-MS 635 (MH$^+$).

H) D-hPro-Pro-Arg-H.2HCl.1.5 H$_2$O

Cbz-D-hPro-Pro-Arg(Cbz)-H (G) (14.0 g, 22.0 mmol) was dissolved in ethanol (150 mL), water (50 mL), and 1N HCl (55 mL). To the solution was added 5 percent Pd/C (5.0 g) and the reaction was hydrogenated at ambient temperature and pressure for 3 hours and the reaction purged with nitrogen for 5 minutes. The catalyst was removed by filtration through a diatomaceous earth pad and the filtrate concentrated in vacuo down to 100 mL. An additional 50 mL of H$_2$O was added to the reaction and pH of solution adjusted to 4.0 with BioRad AG1-X8 resin (hydroxide form). The resin was removed by filtration and the solution lyophilized to give 8.29 g (86 percent) of crude title compound. The crude material in two portions was dissolved in 20 mL 0.05 percent HCl (pH 2.5) and applied to two 5×25 cm columns (Vydac C$_{18}$ resin) connected in series. A gradient system consisting of (A) 0.05 percent HCl and (B) CH$_3$CN was used to elute the pure peptide. The gradient used was an increasing concentration of CH$_3$CN from 2 percent to 10 percent. Fractions were collected and pooled on the basis of analytical RPHPLC profile. The combined fractions were adjusted to pH 4.0 using AG1-X8 resin (Bio-Rad analytical anion exchange resin 50–100 mesh) in hydroxide form. The solution was filtered, and the filtrate was lyophilized to dryness resulting in pure title compound (3.1 g; 61 percent yield):

FAB-MS 367 (MH$^+$);

Amino acid analysis: hPro, 1.00; Pro, 0.98;

$[\alpha]_D$=−88.4° (C=0.5/0.1N HCl);

Elemental Analysis calculated for C$_{17}$H$_{30}$N$_6$O$_3$.2 HCl.1.5 H$_2$O: C 43.78, H 7.56, N 18.02; Found: C 43.48, H 7.25, N 18.00.

The following compounds were synthesized using methods substantially equivalent to those described in Example 1 above or as described elsewhere herein.

EXAMPLE 2

Preparation of D-Prolinyl-L-Prolinyl-L-Arginine Aldehyde Dihydrochloride (D-Pro-Pro-Arg-H.2HCl)

Elemental Analysis calculated for C$_{16}$H$_{30}$N$_6$O$_3$Cl$_2$: C 45.18, H 7.11, N 19.76; Found: C 44.96, H 6.90, N 19.56.

EXAMPLE 3

Preparation of D-Homoprolinyl-L-Azetidinyl-L-Arginine Aldehyde Dihydrochloride (D-hPro-Azt-Arg-H.2HCl)

Elemental Analysis calculated for C$_{16}$H$_{34}$N$_6$O$_5$Cl$_2$: C 41.65, H 7.43, N 18.22; Found: C 43.05, H 7.35, N 18.37.

EXAMPLE 4

Preparation of D-Thiazolidinyl-4-Carbonyl-L-Prolinyl-L-Arginine Aldehyde Dihydrochloride

FAB-MS 371 (MH$^+$);

$[\alpha]_D$=−36.2° (C-0.5/0.1N HCl).

EXAMPLE 5

Preparation of D-2-Isopropyl-5,5-Dimethylthiazolidinyl-4-Carbonyl-L-Prolinyl-L-Arginine Aldehyde Dihydrochloride A) D-2,2,5,5-Tetramethylthiazolidine A solution of D-penicillamine (29.8 g, 0.2 mol) in acetone (1800 mL) was reacted with 12N HCl (18.3 mL) at 50° C. for 4 hours. The reaction mixture was filtered, the filtrate was concentrated down in vacuo to 1500 mL and was allowed to stand at 4° C. for 24 hours. The solid was filtered and dried to give pure title compound (39.1 g, 86 percent yield): mp 188°–191° C.

B) D-5,5-Dimethyl-2-isopropylthiazolidine

A solution of D-2,2,5,5 tetramethylthiazolidine (A) (11.25 g, 0.050 mol) was dissolved in dioxane (150 mL), isobutyraldehyde (14 mL, 0.153 mol) was added and the reaction mixture heated 2 hours at reflux. The reaction mixture was cooled to room temperature and allowed to stand for 24 hours. The precipitate was filtered, and re-crystallized from ethanol (EtOH) (45 mL)/diethyl ether (125 mL) to afford pure title compound (9.0 g, 77 percent yield): mp 214°–216° C.

C) D-2-Isopropyl-5,5-dimethylthiazolidinyl-4-carbonyl-L-prolinyl-L-arginine Aldehyde Dihydrochloride By substantially following the procedures of Steps B through H of Example 1, the title compound was prepared:

FAB-MS 441 (MH$^+$);

$[\alpha]_D$−88°−4° (C=0.5/0.01N HCl);

Elemental Analysis calculated for C$_{20}$H$_{40}$N$_6$O$_4$Cl$_2$S: C 45.20, H 7.57, N 15.81, S 6.03; Found: C 45.44, H 7.39, N 15.86, S 5.87.

EXAMPLE 6

Preparation of trans-4-(2-Naphthyloxy)-D-Prolinyl-L-Prolinyl-L-Arginine Aldehyde Trihydrochloride Monohydrate A) N-Cbz-cis-4-hydroxy-D-proline methyl ester A 5° C. solution of (30 g; 229 mmol) of cis-4-hydroxy-D-proline in 115 mL of 2N aq NaOH was treated simultaneously with 36 mL (252 mmol) of benzyl chloroformate and 115 mL of 2N aq NaOH. After the pH of the reaction had stabilized, the mixture was washed with Et$_2$O (2×150 mL) and was acidified to pH 2 with 5N aq HCl. The reaction was extracted EtOAc (4×200 mL) and the combined EtOAc extracts were dried over Na$_2$SO$_4$ and evaporated in vacuo to give 64.1 g of the crude N-Cbz-protected acid as a gum.

A mixture of the crude acid and 33.0 g (239 mmol) of K$_2$CO$_3$ in 300 mL of DMF was treated with 14.5 mL (233 mmol) of MeI in a dropwise manner. After stirring for 54 hours at room temperature, the reaction was poured into 300 mL of H$_2$O and the mixture extracted with EtOAc (5×200 mL). The combined organic extracts were washed with H$_2$O (3×200 mL), were dried over Na$_2$SO$_4$ and were evaporated in vacuo to give 65.3 g of an oil. Purification by flash chromatography (SiO$_2$; 25 percent EtOAc in hexanes) afforded 47.3 g (169 mmol; 74 percent from cis-4-hydroxy-D-proline) of the title compound as a viscous oil.

FD-MS m/e 279 (M$^+$);

Elemental Analysis calculated for C$_{14}$H$_{17}$NO$_5$: C 60.21, H 6.13, N 5.01; Found: C 59.95, H 6.11, N 4.92.

B) N-Cbz-trans-4-(2-naphthyloxy)-D-proline methyl ester

A solution of 15.0 g (53.7 mmol) of N-Cbz-cis-4-hydroxy-D-proline methyl ester, 11.3 g (78.4 mmol) of β-naphthol, and 20.5 g (78.2 mmol) of triphenylphosphine in 300 mL of THF was treated with 12.3 mL (78.1 mmol) of diethyl azidodicarboxylate over 0.5 hour. The reaction was stirred at room temperature for 18 hours and was quenched by the addition of 100 mL sat'd aq NaCl. The two layers were separated and the organic solution dried (Na$_2$SO$_4$). Evaporation of the solvent gave 46.2 g of an oil which was purified by flash chromatography (SiO$_2$; gradient of 25 percent to 50 percent EtOAc in hexanes) to afford 15.2 g (37.5 mmol; 70 percent) of the title compound.

FD-MS m/e 405 (M$^+$);

IR (film) 3014, 1749, 1705, 1630, 1422, 1357, 1179, 1121 cm$^{-1}$.

Elemental Analysis calculated for C$_{24}$H$_{23}$NO$_5$: C 71.10, H 5.72, N 3.46; Found: C 71.04, H 5.73, N 3.59.

C) trans-4-(2-naphthyloxy)-D-Proline-L-Proline-L-Arginine Aldehyde Trihydrochloride Monohydrate By substantially following the procedures of Example 1 except using lithium tri-t-butoxyalumino hydride, rather than lithium aluminum hydride, to reduce the coupled amino-protected Arg lactam, N-Cbz-trans-4-(2-naphthyloxy)-D-proline methyl ester was converted to the title compound which was isolated as the trihydrochloride monohydrate.

FAB-MS 495 (MH$^+$);

[α]$_D$=−5.11° (C=0.01, MeOH).

Elemental Analysis calculated for C$_{26}$H$_{39}$Cl$_{13}$N$_6$O$_5$: C 50.21, H 6.32, N 13.51; Found: C 50.11, H 6.07, N 13.72.

EXAMPLE 7

Preparation of (1,7-cis)-3-aza-bicyclo[5.4.0]undecanyl-4-carbonyl-L-prolinyl-L-arginine aldehyde dihydrochloride

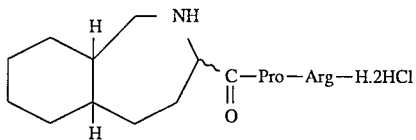

A) 2.Methoxycarbonyl-2,3,4,5-tetrahydro-1H-2-benzazepine-3-carboxylic acid ethyl ester i) α-Tetralone-2-carboxylic acid ethyl ester

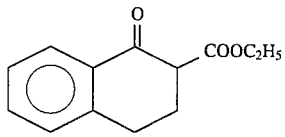

As described by I. Ugi et al. (*J. Liebigs Ann. Chem.* 641, 63 (1961)), α-tetralone is acylated with diethyl oxalate using sodium ethoxide in absolute ethanol; and the resulting ester is thermally decarbonylated to afford the named compound, using the method of C.-J. Lu and F. F. Blicke (*Chem. Abstr.* 52: 11086e).

ii) 1-Oxo-2,3,4,5-tetrahydro-1H-2-benzazepine-3-carboxylic acid ethyl ester

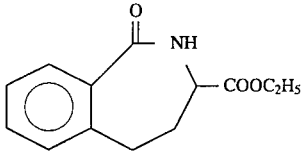

As described by M. Vincent, et al. (U.S. Pat. No. 5,190,823 (1993); European Patent Application, Publication No. 462884 (1991)), the substituted α-tetralone is converted into the named benzazepine using sodium azide and concentrated sulfuric acid in chloroform using the method of C.-J. Lee and F. F. Blicke (*Chem. Abstr.* 5–2: 11086e–f).

iii) 1-Thioxo-2,3,4,5-tetrahydro-1H-2-benzazepine-3-carboxylic acid ethyl ester

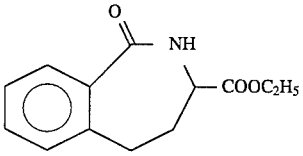

According to the method of Morisawa, et al. (Jpn. Kokai Tokkyo Koho JP 61 57599 [86 57,559] (1986); *Chem. Abstr.* 105: 97354r) the oxobenzazepine is converted into the thioxobenzazepine. Thus, 1-oxo-2,3,4,5-tetrahydro-1H-2-benzazepine-3-carboxylic acid ethyl ester (20 g) dissolved in anhydrous tetrahydrofuran (250 ml) is treated with phosphorous pentasulfide (3.80 g), and the resulting mixture is heated to reflux for 4 hours. Following filtration of insoluble matter, the solution is evaporated and the residue purified by chromatography over silica gel, eluting with 1:2 v/v ethyl acetate:hexane, to afford the thioxo compound as yellow needles (mp 78°–81° C., 71% yield reported).

iv) 2,3,4,5-Tetrahydro-1H-2-benzazepine-3-carboxylic acid ethyl ester

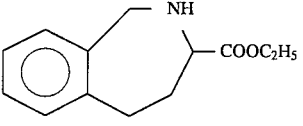

According to the method of Morisawa et al., the thioxo group is reduced from the ring. Thus, 1-thioxo-2,3,4,5-tetrahydro-1H-2-benzazepine-3-carboxylic acid ethyl ester (1.50 g) is dissolved in anhydrous ethanol (200 ml). Raney nickel (30 g) is added, and the resulting mixture is agitated 30 minutes at room temperature. After insoluble matter is filtered, the solution is evaporated, and the residue is purified by chromatography over silica gel, eluting with 1:2 v/v ethyl acetate:hexane, to afford the benzazepine is a light brown oily substance (78% yield reported).

v) 2-Methoxycarbonyl-2,3,4,5-tetrahydro-1H-2-benzazepine-3-carboxylic acid ethyl ester

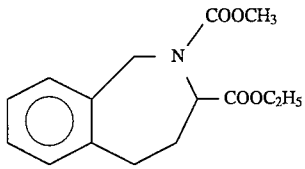

Using a method similar to that described in Example 8-A, the benzazepine is acylated with methyl chloroformate.

B) 2-Methoxycarbonyl-2,3,4,5-tetrahydro-1H-2-benzazepine-3-carboxylic acid

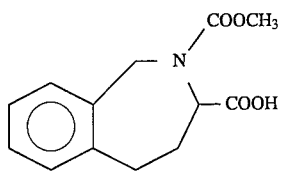

The ethyl ester is conveniently hydrolyzed by treatment of a solution of 10 g ester in THF (100 mL) and water (10 mL) with an equimolar portion of 2N NaOH, followed by stirring overnight at room temperature. The reaction mixture is diluted with diethyl ether (200 mL) and water (100 mL). After the phases are separated, ethyl acetate (200 mL) is added to the aqueous phase, and the solution is acidified to pH 2.0 with 3N HCl. The organic phase is separated, dried (MgSO$_4$) and evaporated to afford the named acid.

The acid may be resolved by a conventional method for preparation of chiral products.

C) 3-Methoxycarbonyl-(1,7-cis)-3-azabicylco[5.4.0]undecane-4-carboxylic acid

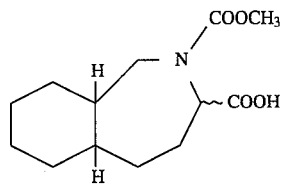

Using a similar method to that described in Example 8-C, the tetrahydrobenzazepine is hydrogenated to afford the perhydro compound.

D) 3-Cbz-(1,7-cis)-3-azabicyclo[5.4.0]undecane-4-carboxylic acid

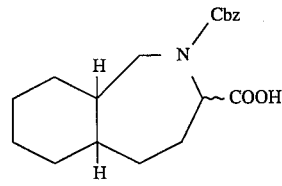

Using a similar procedure to that described in Example 8-D, the methoxycarbonyl group is replaced with a Cbz group.

E) 3-Cbz-(1,7-cis)-3-azabicyclo[4.5.0]undecanyl-4-carbonyl-Pro-O-t-butyl

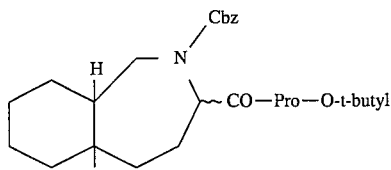

Using a similar procedure to that described in Example 8-D, the acid is coupled with L-Pro-O-t-butyl.

F) 3-Cbz-(1,7-cis)-3-azabicyclo[5.4.0]undecanyl-4-carbonyl-Pro-OH

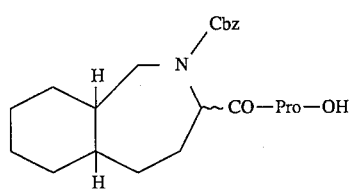

Using a similar procedure to that described in Example 8-F, the carboxy group is deprotected.

G) 3-Cbz-(1,7-cis)-3-azabicyclo[5.4.0]undecanyl-4-carbonyl-Pro-Arg(Cbz)-lactam

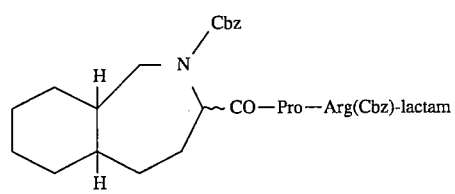

Using a similar procedure to that described in Example 8-G, the acid is coupled to Arg(Cbz)-Lactam.

H) 3-Cbz-(1,7-cis)-3-azabicyclo[5.4.0]undecanyl-4-carbonyl-Pro-Arg-(Cbz) aldehyde

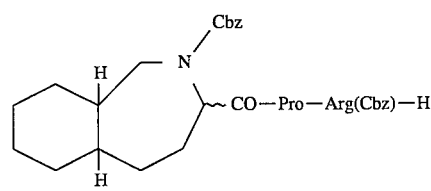

Using a similar procedure to that described in Example 8-H, the lactam is reduced to afford the aldehyde.

I) (1,7-cis)-3-aza-bicyclo[5.4.0]undecanyl-4-carbonyl-L-prolinyl-L-arginine aldehyde dihydrochloride Using a similar method to that described in Example 8-I, the Cbz groups are removed and the title product is purified.

EXAMPLE 8

Preparation of DL-cis-3-aza-bicyclo[5.4.0]undecanyl -2-carbonyl-L-prolinyl-L-arginine aldehyde dihydrochloride

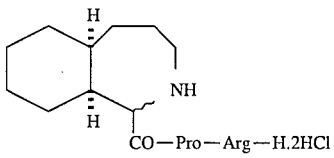

CO—Pro—Arg—H.2HCl

A) N-methoxycarbonyl-3-phenyl-1-propylamine

A stirred solution of 3-phenyl-1-propylamine (19.6 g, mmol) in THF (50 mL) and water (50 mL) was adjusted to pH 9.0 with 2N NaOH. To the reaction was added methyl chloroformate (12.3 mL, 159 mmol) dropwise while the pH was maintained at 9.0 with 2N NaOH. After the reaction was stirred for an additional 30 minutes at room temperature, ethyl acetate (250 mL) was added. The organic layer was separated, dried (MgSO$_4$), filtered, and the filtrate was concentrated in vacuo to give a clear oil of pure title compound (28 g, 100 percent yield):

FAB-MS 193 (M$^+$);

TLC R$_f$ (C) 0.83.

B) Moc-DL-2-carboxy-3,4-benzohomopiperidine

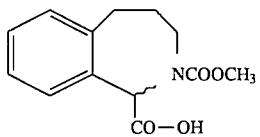

To a solution of N-methoxycarbonyl-3-phenyl-1-propylamine (A) (24.1 g, 125 mmol) in trifluoroacetic acid (125 mL) was added glyoxylic acid (11.1 g, 150 mmol) and heated to reflux temperature. After 4 hours at reflux the reaction was cooled to room temperature, the solvent was removed in vacuo, and diethyl ether (200 mL)/water (50 mL) was added to the residue. The reaction mixture pH was raised to 9.3 with 5N NaOH and the aqueous layer was separated. To the aqueous layer was added ethyl acetate (250 mL), and the solution was acidified to pH 2.5 with 3N HCl. The organic layer was separated, dried (MgSO$_4$), filtered, and the filtrate was concentrated in vacuo to afford an oil of pure title compound (26.9 g, 86 percent yield);

FAB-MS 250 (MH$^+$);

Elemental Analysis calculated for C$_{13}$H$_{15}$NO$_4$: C 62.64, H 6.07, N 5.62; Found: C 62.72, H 6.02, N 5.87.

c) Moc-DL-cis-3-aza-2-carboxybicyclo[5,4,0]undecane

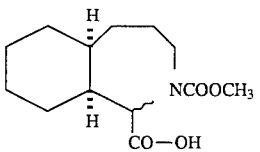

A solution of B (31.5 g, 126 mmol) in EtOH (400 mL) was reacted with hydrogen over 5 percent Rh/Al$_2$O$_3$ (16.0 g) at 138 bar (2000 psi) in a high pressure apparatus at 160° C. for 16 hours. The reaction mixture was filtered through a diatomaceous earth pad, and the filtrate was concentrated in vacuo to give pure title compound (27.8 g, 87 percent yield)

FAB-MS 256 (MH$^+$).

D) Cbz-DL-cis-3-aza-2-carboxybicyclo[5,4,0]undecane

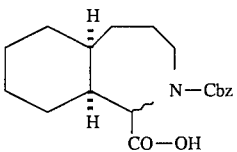

To a stirred solution of C (27.8 g, 109 mmol), at room temperature, in anhydrous CH$_3$CN (200 mL) under an inert atmosphere was added a solution of iodotrimethylsilane (35.7 mL, 250 mmol) in CH$_3$CN (20 mL). The reaction was stirred at 45° C. for 30 minutes and cooled to room temperature. The reaction was quenched with water (200 mL) followed by sodium metabisulfite (1 g). The pH of the reaction was raised to 9.5 with 5N NaOH and benzyl chloroformate (14.4 mL, 101 mmol) was added dropwise while the pH maintained at 9.5 with 2N NaOH. After the reaction was stirred for an additional 30 minutes at room temperature the organic solvent was evaporated in vacuo, and ethyl acetate (200 mL) was added, and the solution was acidified to pH 2.5 with 5N HCl. The organic layer was separated, dried (MgSO$_4$), filtered, and the filtrate was concentrated in vacuo to give a crude oil (31.8 g). The crude oil was purified by chromatography on silica gel using a step gradient elution (CHCl$_3$ 100 percent to CHCl$_3$/EtOAc 1:1) to yield an oil (18.2 g, 50 percent yield). To a stirred, cooled (0° C.) solution of the oil (18.2 g) in THF (100 mL) and water (50 mL) was added 2N NaOH (25.3 mL, 50.6 mmol). The reaction was stirred 24 hour at room temperature. The reaction was diluted with diethylether (200 mL) and water (100 mL). The aqueous layer was separated, EtOAc (200 mL) was added, and the solution was acidified to pH 2.0 with 5N HCl. The organic layer was separated, dried (MgSO$_4$), filtered, and the filtrate was concentrated in vacuo to give pure title compound as an oil (6.9 g, 40 percent yield);

FAB-MS 332 (MH$^+$);

Elemental Analysis calculated for C$_{19}$H$_{25}$NO$_4$: C 68.86, H 7.60, N 4.23; Found: C 68.26, H 7.57, N 4.12.

E) Cbz-DL-cis-3-aza-bicyclo[5,4,0]undecanyl-2-carbonyl-Pro-O-t-butyl

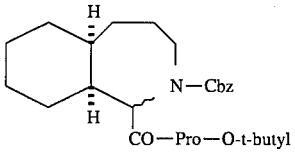

To a stirred, cooled (0° C.) solution of D (6.7 g, 20.2 mmol) in DMF (60 mL) was added L-Pro-O-t-butyl (3.46 g, 20.2 mmol), HOBT (2.73 g, 20.2 mmol), and DCC (4.17 g, 20.2 mmole). The reaction mixture was stirred for 2 hours at 0° C. and warmed to room temperature and stirred (24 h). The reaction mixture was concentrated to dryness in vacuo and the residue was dissolved in EtOAc. The organic solution was washed sequentially with 1N NaHCO$_3$ (100 ml), water, 1.5N citric acid, and water. The organic layer was dried (MgSO$_4$), filtered, and concentrated to dryness in vacuo to give the title pure compound (9.2 g, 94 percent yield):

TLC R$_f$ (A) 0.74;

FAB-MS 484 (M$^+$).

F) Cbz-DL-cis-3-aza-bicyclo[5,4,0]undecanyl-2-carbonyl-Pro-OH

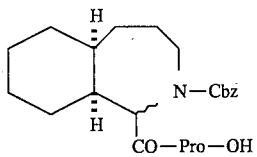

To a stirred, cooled (0° C.) solution of E (9.2 g, 19 mmole) in CH$_2$Cl$_2$ (20 mL), anisole (2.5 ml) was added trifluoroacetic acid (50 ml). The reaction was stirred 1 hour at room temperature. The reaction was concentrated in vacuo without heating and diluted with diethylether (200 mL) and water (200 mL). The pH of the solution was adjusted to 9.8 with 5N NaOH. The aqueous layer was separated, ethyl acetate (250 mL) was added, and the solution was acidified to pH 2.8 with 5N HCl. The organic layer was separated, dried (MgSO$_4$), filtered, and the filtrate was concentrated in vacuo to give the title compound (7.7 g, 95 percent yield) as a clear oil.

TLC R$_f$ (A) 0.75;

FAB-MS 429 (MH+).

G) Cbz-DL-cis-3-azabicyclo[5,4,0]undecanyl-2-carbonyl-Pro-Arg(Cbz)lactam

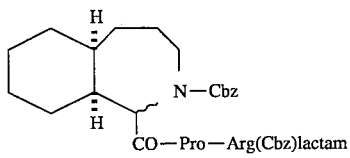

In flask 1 compound F (7.4 g, 17.3 mmole) was dissolved in DMF (50 ml), cooled to −15° C., and N-methylmorpholine (1.9 ml, 17.3 mmole) was added followed by isobutylchloroformate (2.3 ml, 17.3 mmole). The reaction mixture was stirred at −15° C. for 2 minutes. In flask 2 HCl.Arg(Cbz)-Lactam (5.7 g, 17.3 mmole) prepared substantially as described in Example 1, steps D and E, was dissolved in DMF (40 ml), cooled to 0° C., and diisopropylethylamine (7.5 ml, 43.2 mmole) was added to the solution. The reaction mixture was stirred at 0° C. for 2 minutes.

The contents of flask 2 was added to flask 1, and the reaction mixture was stirred for 2 hours (−15° C.) followed by 24 hour at room temperature. The reaction solvent was removed in vacuo to an oil. The residue was dissolved in EtOAc (200 ml) and washed sequentially with 1N NaHCO$_3$ (100 ml), water, 1.5N citric acid, and water. The organic solution was dried (MgSO$_4$), filtered, and concentrated to dryness in vacuo to give a crude solid. The crude solid was purified by chromatography on silica gel using a step gradient elution (hexanes 100 percent to hexane-EtOAc 20:80) to yield as the slower running material pure title compound (2.1 g, 17 percent yield):

FAB-MS 701 (MH$^+$);

Elemental Analysis calculated for C$_{38}$H$_{48}$N$_6$O$_7$: C 65.12, H 6.90, N 11.99; Found: C 65.58, H 7.26, N 11.13.

H) Cbz-DL-cis-3-aza-bicyclo[5,4,0]undecanyl-2-carbonyl-Pro-Arg(Cbz) aldehyde

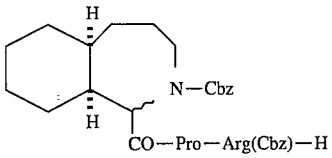

To a stirred, cooled (−70° C.) solution of G (2.1 g, 3.0 mmol) under a N2 atmosphere in anhydrous THF (30 mL) was added lithium aluminum hydride 1M in THF (3.0 mL, 3.0 mmol). The reaction was stirred for 30 min at −70° C. A solution of 5 mL of THF and 5 mL of 0.5N H$_2$SO$_4$ was added dropwise to the reaction. The reaction was diluted with EtOAc (100 mL) and water (50 mL). The organic layer was separated, dried (MgSO$_4$), and filtered. The organic solvent was removed in vacuo to give an amorphous solid of the title compound (2.0 g, 95 percent):

FAB-MS 703 (MH$^+$).

I) DL=cis-3-aza-bicyclo[5,4,0]undecanyl-2-carbonyl-L-prolinyl-L-arginine aldehyde dihydrochloride

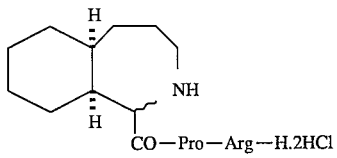

Compound H (2.0 g 2.8 mmol) dissolved in ethanol (120 mL), water (30 mL), and 1N HCl (7.0 mL, 7.0 mmol) was hydrogenated in the presence of 5 percent Pd/C catalyst (1.5 g) at ambient temperature and pressure. After the reaction was completed, the catalyst was removed by filtration. The filtrate was concentrated down to 30 mL in vacuo and water (50 mL) was added. The pH of the solution was adjusted to 4.0 with BioRad AG1-X8 resin (hydroxide form). The resin was removed by filtration and the solution lyophilized to give the title compound (1.27 g, 89 percent):

FAB-MS 435 (MH$^+$);

Elemental Analysis calculated for C$_{22}$H$_{38}$N$_6$O$_3$.2HCl.3H$_2$O: C 46.31, H 8.30, N 14.73; Found: C 46.10, H 7.94, N 14.43.

EXAMPLE 9

Preparation of D,L-Piperazin-2-oyl-L-Prolinyl-L-Arginine Aldehyde Dihydrochloride The title compound was prepared from D,L-piperazine-2-carboxylic acid dihydrochloride by substantially following the procedures of Example 1 except using lithium tri-t-butoxyaluminohydride, rather than lithium aluminum hydride, to reduce the coupled amino-protected Arg lactam:

FAB-MS m/e 368 (MH$^+$);

Elemental Analysis calculated for C$_{16}$H$_{31}$Cl$_2$N$_7$O$_3$: C 43.64, H 7.10, N 22.26; Found: C 43.17, H 7.78, N 15.21.

EXAMPLE 10

Preparation of D,L-Thiazolidinyl-2-carbonyl-L-prolinyl-L-arginine aldehyde dihydrochloride A) Cbz-D,L-thiazolidinyl-2-carbonyl-L-Prolinyl-L-Arginyl Lactam The title compound was prepared from D,L-thiazolidinyl-2-carboxylic acid by substantially following the procedures described in Example 9.

FD-MS: m/e 636 (M+)

$[\alpha]_D = -74.26°$ (C=0.01, $CH_2Cl_2$)

Elemental Analysis calculated for $C_{31}H_{36}N_6O_7S$: C 58.48, H 5.70, N 13.20; Found: C 58.49, H 5.57, N 12.95.

B) Cbz-D,L-thiazolidinyl-2-carbonyl-L-Proline-Cbz-L-Arginine Aldehyde

A −25° C. solution of 12.3 g (19.0 mmol) of Cbz-D,L-thiazolidinyl-2-carbonyl-L-prolyinyl-L-arginyl lactam in 200 mL THF was treated with 29 mL (1 M in THF; 29 mmol) of Li(t-BuO)$_3$AlH solution at a rate that did not warm the reaction temperature to above −20° C. The reaction was stirred at −25° C. for 3 hours and was poured into 100 mL HCl. The mixture was extracted with 1:1 THF-hexane (2×100 mL) and EtOAc (2×100 mL). The EtOAc layer was dried over $Na_2SO_4$ and evaporated in vacuo to afford 6.96 g (10.9 mmol; 58 percent yield) of the crude product as a white foam. The presence of the desired product was confirmed by mass spec. [FD-MS; m/e 638 (M+)] and the mixture taken on to the next reaction without further purification.

C) D,L-thiazolidinyl-2-carbonyl-L-prolinyl-L-arginine aldehyde dihydrochloride

To a mixture of the protected aldehyde (B) (6.72 g; 10.5 mmol) and p-cresol (7.0 mL) was added 35 mL of liquid HF in a Teflon/Kel-F apparatus. The mixture was stirred at 0° C. for 20 min, and then the HF was removed in vacuo. The residue was triturated with $Et_2O$ to give a white solid which was purified by reverse phase chromatography using a 5×25 cm Vydac $C_{18}$ RPHPLC column using a gradient of 2 percent $CH_3CN$ in 0.5 percent aq HCl to 40 percent $CH_3CN$ in 0.5 percent aq HCl. The pure fractions were combined and lyopholized to afford 2.65 g (6.0 mmol; 60 percent) of the title compound as the dihydrochloride.

FAB-MS m/e 370 (M+)

Elemental Analysis calculated for $C_{15}H_{28}Cl_2N_6O_3S$: C 40.63, H 6.37, N 18.95; Found: C 40.84, H 6.19, N 18.80.

EXAMPLE 11

Preparation of
D,L-thiomorpholinyl-2-carbonyl-L-Proline-L-Arginine Aldehyde Dihydrochloride The title compound was prepared by substantially following the procedure used in the synthesis of D,L-thiazolidinyl-2-carbonyl-L-proline-arginine aldehyde dihydrochloride (Example 10):

FAB-MS m/e 385 (M+);

$[\alpha]_D = -58° - 43°$ (C=0.01, MeOH);

Elemental Analysis calculated for $C_{16}H_{30}Cl_2N_6O_3S$: C 42.01, H 6.61, N 18.37; Found: C 40.73, H 6.73, N 15.09.

EXAMPLE 12

Preparation of D-Cis-(4-phenoxy) Prolinyl-L-Prolinyl-L-Arginine Aldehyde Trihydrochloride Monohydrate By substantially following the procedures of Example 6, the title compound was prepared:

FAB-MS 445 (MH+);

Elemental Analysis calculated for $C_{22}H_{32}N_6O_{4.3}$ HCl.$H_2O$ C 46.20, H 6.52, N 14.69; Found: C 46.04, H 6.73, N 14.44.

EXAMPLE 13

Preparation of
4-(3-pyridyloxy)-D-prolinyl-L-prolinyl-L-arginine aldehyde hydrochloride hydrate A) N-CBz-trans-4-(3-pyridyloxy)-D-Proline Methyl Ester The title compound was prepared from 3-hydroxy pyridine and N-Cbz-cis-4-hydroxy-D-proline methyl ester by substantially following the procedure used in the preparation of N-Cbz-trans-4-(2-naphthyloxy)-D-proline methyl ester, Example 6, Steps A and B.

FD-MS 356 (M+);

Elemental Analysis calculated for $C_{19}H_2ON_2O_5$: C 64.04, H 5.66, N 7.86; Found: C 64.22, H 5.81, N 7.76.

B) 4-(3-pyridyloxy)-D-Proline-L-Proline-Arginine Aldehyde Hydrochloride Hydrate

The title compound was prepared from N-Cbz-trans-4-(3-pyridyloxy)-D-proline methyl ester by substantially following the procedures of Example 9.

FAB -MS 368 (M+);

Elemental Analysis calculated for $C_{21}H_{34}ClN_7O_5$: C 50.45, H 6.38, N 19.61; Found: C 50.62, H 6.61, N 19.60.

EXAMPLE 14

Preparation of
trans-4-phenylthio-D-prolinyl-L-prolinyl-L-arginine aldehyde trihydrochloride trihydrate A) N-Cbz-cis-4-tosyl-D-proline methyl ester A solution of 20 g (71.6 mmol) of N-Cbz-cis-4-hydroxy-D-proline methyl ester, 15 mL (107 mmol) of triethylamine and 0.4 g (3.3 mmol) of 4-dimethylaminopyridine in 200 mL of $CHCl_3$ was treated with 15.1 g (79.2 mmol) of p-toluenesulfonyl chloride in portions. The reaction was stirred at room temperature for 18 hours and was washed successively with 100 mL of $H_2O$, 100 mL of 1N aqueous citric acid, and 100 mL of $H_2O$. The organic fraction was dried over $Na_2SO_4$ and evaporated in vacuo to give 31.4 g of an oil which was purified by flash chromatography ($SiO_2$; 50 percent EtOAc in hexanes) to afford 18.2 g (42 mmol; 59 percent) of the title compound as a white solid.

FD-MS m/e 433 (M+);

Elemental Analysis calculated for $C_{21}H_{23}NO_7S$: C 58.19, H 5.35, N 3.23; Found: C 58.43, H 5.33, N 3.16.

B) N-Cbz-trans-4-Phenylthio-D-Proline ethyl ester

Thiophenol (3.3 mL; 32.2 mmol) was added to a solution of 35.6 mmol of sodium ethoxide in 40 mL EtOH (generated from adding 820 mg of Na to 40 mL EtOH). The mixture was stirred for 15 min and was treated with 6.0 g (15 mmol) of solid N-Cbz-cis-4-tosyl-D-proline methyl ester. The reaction was stirred at 40° C. for 19 hours at which time it was cooled and diluted with 100 mL of $H_2O$. The EtOH was evaporated in vacuo and the aqueous layer extracted with EtOAc (3×100 mL). The combined organic extracts were dried over $Na_2SO_4$ and evaporated in vacuo to give 7.40 g of an oil which was purified by flash chromatography ($SiO_2$; 5 percent EtOAc in hexanes) to afford 4.60 g (12 mmol; 79 percent) of the title compound as a clear oil.

FD-MS m/e 385 (M+);

Elemental Analysis calculated for $C_{14}H_{17}NO_5$: C 65.43, H 6.01, N 3.63; Found: C 65.39, H 6.01, N 3.85.

C) trans-4-Phenylthio-D-Proline-L-Proline-Arginine Aldehyde Trihydrochloride Trihydrate The title compound was prepared from N-Cbz-trans-4-phenylthio-D-proline ethyl ester by substantially following the procedures used in the synthesis of D,L-thiazolidinyl-2-carbonyl-L-Proline-L-Arginine Aldehyde dihydrochloride, Example 10.

FAB-MS m/e 461 (M+).

High Resolution Mass Spec. (HRMS) (MH+), $C_{22}H_{33}N_6O_3S$. Theory 461.2341, Found: 461.2318.

Elemental Analysis calculated for $C_{22}H_{35}Cl_3N_6O_3S.3H_2O$: C 42.35, H 6.62, N 13.47; Found: C 42.46, H 5.73, N 13.53.

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents' without substantial interference with thrombolysis and fibrinolysis.

The invention in one of its aspects provides a method of inhibiting thrombin in meals comprising administering to a mammal in need of treatment an effective (thrombin inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in mammals comprising administering to a mammal in need of treatment an effective (coagulation inhibiting) dose of a compound of formula I.

The thrombin inhibition, coagulation inhibition and thromboembolic disorder treatment contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally, parenterally e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 ml sterile glass ampoule. Another example of a unit dosage formulation comprises about 10 mg of a compound of the present invention as a pharmaceutically acceptable salt in 20 ml of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Another embodiment of the present invention is a pharmaceutical formulation comprising an effective amount of a compound of Formula I or a pharmaceutically acceptable salt or solvate thereof in association with a pharmaceutically acceptable carrier, diluent or excipient therefor.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt or solvate thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
| --- | --- |
| Starch | 59 mg |
| Microcrystalline cellulose | 59 mg |

| | |
|---|---|
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Isotonic saline | 1,000 ml |

The solution of the above ingredients generally is administered intravenously to a subject at a rate of 1 ml per minute.

The ability of the compounds of the present invention to be an effective and orally active thrombin inhibitor are evaluated in one or more of the following assays.

The compounds provided by the invention (formula 1) selectively inhibit the action of thrombin in mammals. The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide, N-benzoyl-L-Phe-L-Val-L-Arg-p-nitroanilide.

The assay is carried out by mixing 50 μl buffer (0.03M Tris, 0.15M NaCl, pH 7.4) with 25 μl of human thrombin solution (purified human thrombin, Enzyme Research Laboratories, South Bend, Ind., at 8 NIH units/ml) and 25 μl of test compound in a solvent (50% aqueous methanol (v:v)). Then 150 μl of an aqueous solution of the chromogenic substrate (at 0.25 mg/ml) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

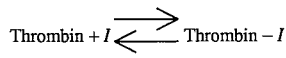

$$Kass = \frac{[\text{Thrombin} - I]}{[(\text{Thrombin}) \times (I)]}$$

Kass is calculated for a range of concentrations of test compounds and the mean value reported in units of liter per mole.

By substantially following the procedures described above for human thrombin, and using other human blood coagulation system serine proteases and using fibrinolytic system serine proteases, with the appropriate chromogenic substrates, identified below, the selectivity of the compounds of the present invention with respect to the coagulation factor serine proteases and to the fibronolytic serine proteases are evaluated as well as their substantial lack of interference with human plasma clot fibrinolysis.

Human factors X, Xa, IXa, XIa, and XIIa are purchased from Enzyme Research Laboratories, South Bend, Ind.; human urokinase from Leo Pharmaceuticals, Denmark; and recombinant activated Protein C (aPC) is prepared at Eli Lilly and Co. substantially according to U.S. Pat. No. 4,981,952. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from KabiVitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants, or purchaed from Midwest Biotech, Fishers, Ind.

Human plasmin is purchased from Boehringer Mannheim, Indianapolis, Ind.; nt-PA is purchased as single chain activity reference from American Diagnostica, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Table 1 which follows lists the Kass values obtained with the indicated compound represented by formula I.

TABLE 1

| Human Thrombin Inhibition Levels | |
|---|---|
| Example | Kass × $10^6$ (l/mole) |
| 1 | 46 |
| 2 | 12 |
| 3 | 45 |
| 4 | 5 |
| 5 | 4 |
| 6 | 21 |
| 8 | 595 |
| 9 | 121 |
| 10 | 27 |
| 12 | 25 |
| 13 | |
| 14 | 37 |

Thrombin inhibitors preferably should spare fibrinolysis induced by urokinase, tissue plasminogen activator (t-PA) and steptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agents. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Hazelton-LRE, Kalamazoo, Mich., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased form Leo Pharmaceuticals, Denmark, as 2200 Ploug units/vial. Streptokinase is purchased from Hoechst-Roussel Pharmaceuticals, Somerville, N.J. Methods—Effects on Lysis of Human Plasma Clots by t-PA Human plasma clots are formed in micro test tubes by adding 50 ul thrombin (73 NIH unit/ml) to 100 ul human plasma which contains 0.0229 uCi 125-iodine labeled fibrinogen. Clot lysis is studied by overlaying the clots with 50 ul of urokinase or streptokinase (50, 100, or 1000 unit/ml) and incubating for 20 hours at room temperature. After incubation the tubes are centrifuged in a Beckman Microfuge. 25 ul of supernate is added into 1.0 ml volume of 0.03M tris/0.15M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 ug/ml concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, hazelton-LRE, Kalamazoo, Mich., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents ACTIN, Thromboplastin, and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 ml saline and 0.05 ml Thromboplastin-C reagent to 0.05 ml test plasma. The activated partial thromboplastin time (APTT) is measured by incubation of 0.05 ml test plasma with 0.05 ml Actin reagent for 120 seconds followed by 0.05 ml $CaCl_2$ (0.02M). The thrombin time (TT) is measured by adding 0.05 ml saline and 0.05 ml thrombin (10 NIH units/ml) to 0.05 ml test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, IN) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous shunt model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

$FeCl_3$ model of arterial injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 ul is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, *Thromb. Res.*, 60:269,1990).

Spontaneous thrombolysis model

In vitro data suggests that peptide thrombin inhibitors inhibit thrombin and at higher concentration may inhibit, other serine proteases, such as plasmin and tissue plasminogen activator. To assess if the compounds inhibit fibrinolysis in vivo, the rate of spontaneous thrombolysis is determined by implanting a labeled whole blood clot into the pulmonary circulation. Rat blood (1 ml) is mixed rapidly with bovine thrombin (4 IU, Parke Davis) and $^{125}I$ human fibrogen (5 µCi, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected } cpm - \text{lung } cpm)}{\text{injected } cpm} \times 100$$

The fibrinolytic dissolution of the implanted clot occurs time-dependently (see J. P. Clozel, *Cardiovas. Pharmacol.*, 12:520, 1988).

Coagulation parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 ml) is mixed with saline (0.1 ml) and bovine thrombin (0.1 ml, 30 U/ml in TRIS buffer; Parke Davis) at 37° C. For APTT, plasma (0.1 ml) and APTT solution (0.1 ml, Organon Teknika) are incubated for 5 minutes (37° C.) and $CaCl_2$ (0.1 ml, 0.025M) is added to start coagulation. Assays are done in duplicate and averaged.

Index of Bioavailability

A measure of bioactivity, plasma thrombin time (TT), serves as a substitute for the assay of parent compound on the assumption that increments in TT resulted from thrombin inhibition by parent only. The time course of the effect of the thrombin inhibitor upon TT is determined after i.v bolus administration to anesthetized rats and after oral treatment of fasted conscious rats. Due to limitations of blood volume and the number of points required to determine the time course from time of treatment to the time when the response returns to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{AUC\, po}{AUC\, iv} \times \frac{\text{Dose } iv}{\text{Dose } po} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Bolus injection volume is 1 ml/kg for i.v., and 5 ml/kg for p.o. and infusion volume is 3 ml/hr.

Statistics

Results are expressed as means ±SEM. One-way analysis of variance is used to detect statistically significant differences and then Dunnett's test is applied to determine which means are different. Significance level for rejection of the null hypothesis of equal means is $P<0.05$.

TABLE 2

| | Index of Bioavailability |
|---|---|
| Example | Percent Relative Activity |
| 1 | 38% |
| 2 | 36% |
| 3 | 32% |
| 4 | 16% |
| 5 | |
| 6 | |
| 8 | 43% |
| 9 | 19% |
| 10 | 5% |
| 11 | |
| 12 | 16% |
| 13 | |
| 14 | |

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Miss.) 240 minutes after dosing. Water is available ad libitum. The room temperature is maintained between 66°–74° F.; 45–50 percent relative humidity; and lighted from 0600–1800 hours.

Pharmacokinetic model.

Test compound is formulated immediately prior to dosing by dissolving in sterile 0.9 percent saline to a 5 mg/ml preparation. Dogs are given a single 2 mg/kg dose of test compound by oral garage. Blood samples (4.5 ml) are taken from the cephalic vein at 0.25, 0.5, 0.75, 1,2,3,4 and 6 hours after dosing. Samples are collected in citrated Vacutainer tubes and kept on ice prior to reduction to plasma by centrifugation. Plasma samples are derivatized with dinitrophenylhydrazine and analyzed by HPLC (Zorbax SB-$C_8$ column) eluting with methanol/500 mM sodium acetate adjusted to $pH_7$ with phosphoric acid (60:40, v/v). Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

TABLE 3

| | | Pharmacokinetic Parameters | | | | |
|---|---|---|---|---|---|---|
| Example | Ke (min-1) | Clt/F (L/hr · kg) | VD/F (L/kg) | Tmax (hr) | Cmax (ng/ml) | t0.5 (min) | A.U.C. (ng · hr/ml) o-infinity |
| 1 | 0.0104 ± 0.0009 | 0.437 ± 0.032 | 0.729 ± 0.120 | 1–2 | 1676 ± 202 | 67 range = 57–86 | 4651 ± 319 |

Canine Model of Coronary Artery Thrombosis

Surgical preparation and instrumentation of the dogs are as described in Jackson, et al., *Circulation,* 82, 930–940 (1990). Mixed-breed hounds (aged 6–7 months, either sex, Hazelton-LRE, Kalamazoo, Mich., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment).

The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-μA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for ≧30 minutes.

Hematology and template bleeding time determinations

Whole blood cell counts, hemoglobin, and hematocrit values are determined on a 40-μl sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of p<0.05. All values are mean ±SEM. All studies are conducted in accordance with the guiding principles of the American Physiological Society. Further details regarding the procedures are described in Jackson, et al., *J. Cardiovasc. Pharmacol.,* 21, 587–599 (1993).

TABLE 4

| Canine Model of Coronary Artery Thromboses | | |
|---|---|---|
| Example | Dose mg/kg · hr | Time to Occlusion (min) |
| 1 | 0.25 | 60 |
| | 0.50 | 150 |
| | 1.00 | >225 |

The compound of Example 1 was also evaluated in the Template Bleeding Time assay at 0.25, 0.50 and 1.0 mg/kg.hr. Over a 240 minute time, the compound of Example 1 showed no significant effect on template bleeding time.

We claim:

1. A compound having the formula I

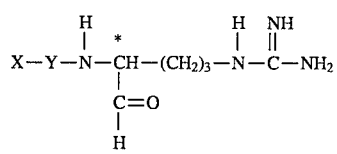

wherein

X is an unsubstituted or substituted group selected from homoprolinyl, prolinyl, thiazolidinoyl, isothiazolidinoyl, thiomorpholinoyl, piperazinoyl, morpholinoyl, oxazolidinoyl, isoxazolidinoyl, 2-azanorbornoyl, and fused bicyclic rings

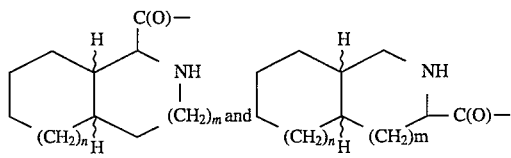

where n is 1–3 and m is 2 or 3 and in a sulfur containing group the sulfur may be oxidized with one or two oxygen atoms;

Y is

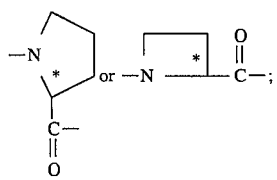

or a pharmaceutically acceptable salt thereof or a pharmaceutically acceptable solvate of said compound or salt thereof;

and further wherein when X is a substituted group selected from homoprolinyl, prolinyl, thiazolidinoyl, isothiazolidinoyl, thiomorpholinoyl, piperazinoyl, morpholinoyl, oxazolidinoyl, isoxazolidinoyl, 2-azanorbornoyl, and fused bicyclic rings,

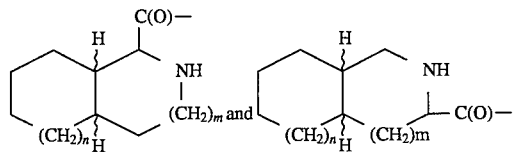

there can be one to three of the same or different substituents that will afford a stable structure selected from halo, hydroxyl, $C_1$–$C_4$ alkyl, $C_1$–$C_4$ alkoxy, amino (—$NH_2$), mono($C_1$–$C_4$ alkyl)amino, di($C_1$–$C_4$ alkyl)amino, mercapto, $C_1$–$C_4$alkylthio (—S(O)$_p$($C_1$–$C_4$ alkyl)), —NHS(O)$_p$($C_1$–$C_4$ alkyl), —NHC(O)$C_1$–$C_4$ alkyl, —S(O)$_p$NH2, —S(O)$_p$NH($C_1$–$C_4$ alkyl), —S(O)$_p$N($C_1$–$C_4$ alkyl)$_2$, substituted or unsubstituted phenoxy, substituted or unsubstituted naphthyloxy, substituted or unsubstituted pyridyloxy, substituted or unsubstituted phenylthio; p is 0, 1 or 2; and the substituents on the phenoxy, naphthyloxy, pyridyloxy and phenyl thio groups are one or two of the same or different substituents selected from halo, hydroxyl, $C_1$–$C_4$ alkyl, $C_1$–$C_4$ alkoxy, amino (—$NH_2$), mono($C_1$–$C_4$ alkyl)amino, di($C_1$–$C_4$ alkyl)amino, mercapto, $C_1$–$C_4$alkylthio (—S(O)$_p$($C_1$–$C_4$ alkyl)), —NHS(O)$_p$($C_1$–$C_4$ alkyl), —NHC(O)$C_1$–$C_4$ alkyl, —S(O)$_p$NH2, —S(O)$_p$NH($C_1$–$C_4$ alkyl), —S(O)$_p$N($C_1$–$C_4$ alkyl)$_2$, and p is 0, 1 or 2.

2. The compound or salt or solvate thereof as claimed in claim 1 wherein X is unsubstituted or monosubstituted homoprolinyl, unsubstituted or monosubstituted prolinyl, unsubstituted or monosubstituted piperazinoyl, or an unsubstituted or monosubstituted fused bicyclic ring selected from

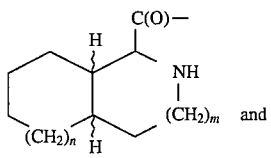

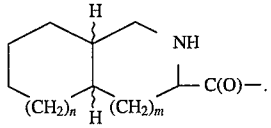

3. The compound or salt or solvate thereof as claimed in claim 2 wherein X is homoprolinyl, prolinyl, 4-phenoxyprolinyl, piperazinoyl, or a fused bicyclic ring selected from

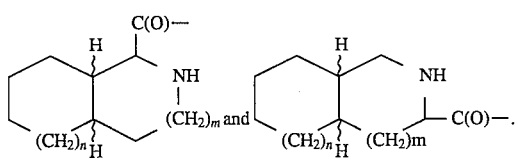

4. The compound or salt or solvate thereof as claimed in claim 1 wherein, alkyl by itself or as part of another substituent is methyl, ethyl, n-propyl, isopropyl, n-butyl, t-butyl, isobutyl or sec-butyl; and halo is chloro, fluoro, bromo or iodo.

5. The compound or salt or solvate thereof as claimed in claim 1 which compound is selected from:

D-homoprolinyl-L-prolinyl-L-arginine aldehyde;

D-prolinyl-L-prolinyl-L-arginine aldehyde;

D-homoprolinyl-L-azetidin-2-carbonyl-L-arginine aldehyde;

D-prolinyl-L-azetidin-2-carbonyl-L-arginine aldehyde; and

D-(4-phenoxy)prolinyl-L-prolinyl-L-arginine aldehyde.

6. A pharmaceutical formulation comprising in association with a pharmaceutically acceptable carrier, diluent, or excipient, a compound of the formula I, or a pharmaceutically acceptable salt or solvate thereof, as claimed in claim 1.

7. The formulation as claimed in claim 6 wherein X is unsubstituted or monosubstituted homoprolinyl, unsubstituted or monosubstituted prolinyl, unsubstituted or monosubstituted piperazinoyl, or an unsubstituted or monosubstituted fused bicyclic ring selected from

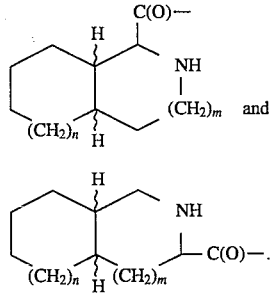

8. The formulation as claimed in claim 7 wherein X is homoprolinyl, prolinyl, 4-phenoxyprolinyl, piperazinoyl, or a fused bicyclic ring selected from

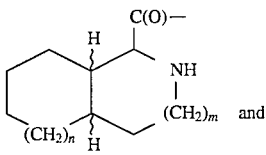

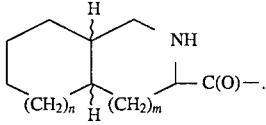

9. The formulation as claimed in claim 6 wherein, alkyl by itself or as part of another substituent is methyl, ethyl, n-propyl, isopropyl, n-butyl, t-butyl, isobutyl or sec-butyl; and halo is chloro, fluoro, bromo or iodo.

10. The formulation as claimed in claim 6 in which said compound is selected from:

D-homoprolinyl-L-prolinyl-L-arginine aldehyde;

D-prolinyl-L-prolinyl-L-arginine aldehyde;

D-homoprolinyl-L-azetidin-2-carbonyl-L-arginine aldehyde;

D-prolinyl-L-azetidin-2-carbonyl-L-arginine aldehyde; and

D-(4-phenoxy)prolinyl-L-prolinyl-L-arginine aldehyde.

11. A method of inhibiting thrombin in a mammal comprising administering an effective dose of a compound of formula I, or a pharmaceutically acceptable salt or solvate thereof, as claimed in claim 1 to a mammal requiring thrombin inhibition.

12. The method as claimed in claim 11 wherein X is unsubstituted or monosubstituted homoprolinyl, unsubstituted or monosubstituted prolinyl, unsubstituted or monosubstituted piperazinoyl, or an unsubstituted or monosubstituted fused bicyclic ring selected from

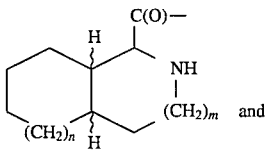

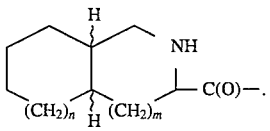

13. The method as claimed in claim 12 wherein X is homoprolinyl, prolinyl, 4-phenoxyprolinyl, piperazinoyl, or a fused bicyclic ring selected from

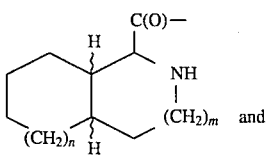

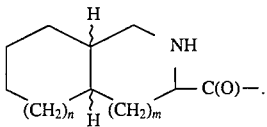

14. The method as claimed in claim 11 wherein, alkyl by itself or as part of another substituent is methyl, ethyl, n-propyl, isopropyl, n-butyl, t-butyl, isobutyl or sec-butyl; and halo is chloro, fluoro, bromo or iodo.

15. The method as claimed in claim 11 in which said compound is selected from:

D-homoprolinyl-L-prolinyl-L-arginine aldehyde;

D-prolinyl-L-prolinyl-L-arginine aldehyde;

D-homoprolinyl-L-azetidin-2-carbonyl-L-arginine aldehyde;

D-prolinyl-L-azetidin-2-carbonyl-L-arginine aldehyde; and

D-(4-phenoxy)prolinyl-L-prolinyl-L-arginine aldehyde.

16. A method of treating thromboembolic disorder in a mammal comprising administering to a mammal requiring thromboembolic disorder treatment an effective dose of a compound of formula I, or a pharmaceutically acceptable salt or solvate thereof, as claimed in claim 1.

17. The method as claimed in claim 16 wherein X is unsubstituted or monosubstituted homoprolinyl, unsubstituted or monosubstituted prolinyl, unsubstituted or monosubstituted piperazinoyl, or an unsubstituted or monosubstituted fused bicyclic ring selected from

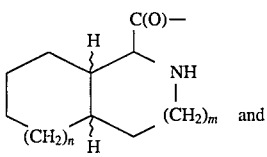

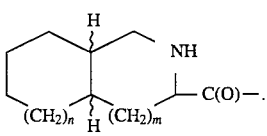

18. The method as claimed in claim 17 wherein X is homoprolinyl, prolinyl, 4-phenoxyprolinyl, piperazinoyl, or a fused bicyclic ring selected from

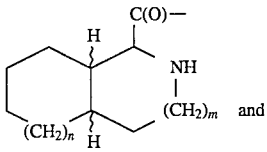

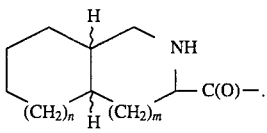

19. The method as claimed in claim 16 wherein, alkyl by itself or as part of another substituent is methyl, ethyl, n-propyl, isopropyl, n-butyl, t-butyl, isobutyl or sec-butyl; and halo is chloro, fluoro, bromo or iodo.

20. The method as claimed in claim 16 in which said compound is selected from:

D-homoprolinyl-L-prolinyl-L-arginine aldehyde;

D-prolinyl-L-prolinyl-L-arginine aldehyde;

D-homoprolinyl-L-azetidin-2-carbonyl-L-arginine aldehyde;

D-prolinyl-L-azetidin-2-carbonyl-L-arginine aldehyde; and

D-(4-phenoxy)prolinyl-L-prolinyl-L-arginine aldehyde.

21. A method of inhibiting coagulation in a mammal comprising administering to a mammal requiring coagulation inhibition an effective dose of a compound of formula I, or a pharmaceutically acceptable salt or solvate thereof, as claimed in claim 1.

22. The method as claimed in claim 21 wherein X is unsubstituted or monosubstituted homoprolinyl, unsubstituted or monosubstituted prolinyl, unsubstituted or monosubstituted piperazinoyl, or an unsubstituted or monosubstituted fused bicyclic ring selected from

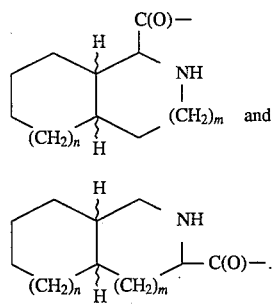

23. The method as claimed in claim 22 wherein X is homoprolinyl, prolinyl, 4-phenoxyprolinyl, piperazinoyl, or a fused bicyclic ring selected from

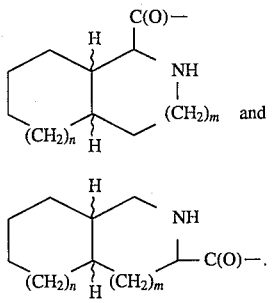

24. The method as claimed in claim 21 wherein, alkyl by itself or as part of another substituent is methyl, ethyl, n-propyl, isopropyl, n-butyl, t-butyl, isobutyl or sec-butyl; and halo is chloro, fluoro, bromo or iodo.

25. The method as claimed in claim 21 in which said compound is selected from:

D-homoprolinyl-L-prolinyl-L-arginine aldehyde;

D-prolinyl-L-prolinyl-L-arginine aldehyde;

D-homoprolinyl-L-azetidin-2-carbonyl-L-arginine aldehyde;

D-prolinyl-L-azetidin-2-carbonyl-L-arginine aldehyde; and

D-(4-phenoxy)prolinyl-L-prolinyl-L-arginine aldehyde.

* * * * *

UNITED STATES PATENT AND TRADEMARK OFFICE
CERTIFICATE OF CORRECTION

PATENT NO. : 5,578,574

DATED : November 26, 1996

INVENTOR(S) : Shuman et al.

It is certified that error appears in the above-indentified patent and that said Letters Patent is hereby corrected as shown below:

At column 16, line 35 delete the formula

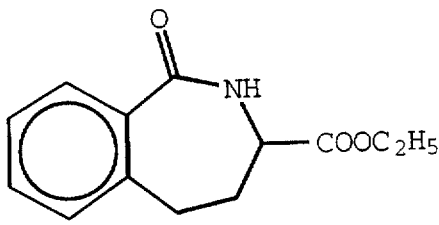

and enter the formula

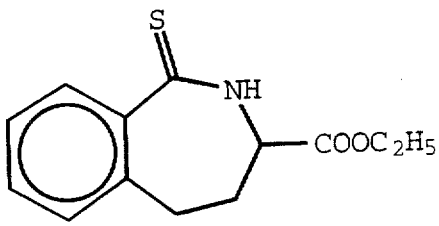

therefor; i.e. replace the oxo "O" with the thioxo "S" at the 1-position of the ring.

Signed and Sealed this

Thirteenth Day of May, 1997

Attest:

BRUCE LEHMAN

Attesting Officer    Commissioner of Patents and Trademarks